(12) United States Patent
Pavlin

(10) Patent No.: US 8,058,386 B2
(45) Date of Patent: Nov. 15, 2011

(54) POLYALKYLENE GLYCOL-BASED POLY(ESTER-AMIDE) POLYMERS, METHODS OF MAKING AND METHODS OF USING SAME, COMPOSITIONS AND PRODUCTS COMPRISING SAME

(75) Inventor: Mark S. Pavlin, Kingsport, TN (US)

(73) Assignee: Arizona Chemical Company, LLC, Jacksonville, FL (US)

( * ) Notice: Subject to any disclaimer, the term of this patent is extended or adjusted under 35 U.S.C. 154(b) by 390 days.

(21) Appl. No.: 12/211,248

(22) Filed: Sep. 16, 2008

(65) Prior Publication Data
US 2010/0069286 A1    Mar. 18, 2010

(51) Int. Cl.
*A61K 9/52*    (2006.01)
*C08G 696/26*    (2006.01)

(52) U.S. Cl. .................. 528/340; 528/332; 528/271
(58) Field of Classification Search .................. 528/340, 528/332
See application file for complete search history.

(56) References Cited

U.S. PATENT DOCUMENTS

| | | | | |
|---|---|---|---|---|
| 3,157,681 A * | 11/1964 | Fischer | ........................ | 562/509 |
| 3,839,245 A * | 10/1974 | Schlossman et al. | ......... | 524/100 |
| 4,230,838 A * | 10/1980 | Foy et al. | ...................... | 525/408 |
| 4,940,577 A * | 7/1990 | Greenberg et al. | ............. | 424/59 |
| 5,783,657 A * | 7/1998 | Pavlin et al. | ................... | 528/310 |
| 5,998,570 A * | 12/1999 | Pavlin et al. | ................... | 528/310 |
| 6,111,055 A * | 8/2000 | Berger et al. | ................... | 528/310 |
| 6,242,509 B1 * | 6/2001 | Berger et al. | ................... | 523/122 |
| 6,268,466 B1 * | 7/2001 | MacQueen et al. | ........... | 528/335 |
| 6,399,713 B1 * | 6/2002 | MacQueen et al. | ........... | 525/408 |
| 6,469,131 B2 * | 10/2002 | Lawson et al. | ................ | 528/335 |
| 6,503,077 B2 * | 1/2003 | Orth et al. | ...................... | 431/288 |
| 6,503,522 B2 * | 1/2003 | Lawson et al. | ................ | 424/401 |
| 6,552,160 B2 * | 4/2003 | Pavlin | ........................ | 528/339.5 |
| 6,592,857 B2 * | 7/2003 | Lawson et al. | ........... | 424/70.122 |
| 6,864,349 B2 * | 3/2005 | Pavlin et al. | ................... | 528/310 |
| 6,870,011 B2 * | 3/2005 | MacQueen et al. | ........... | 525/408 |
| 6,875,245 B2 * | 4/2005 | Pavlin | ............................ | 44/275 |
| 6,956,099 B2 * | 10/2005 | Pavlin | ........................... | 528/310 |
| 7,253,249 B2 * | 8/2007 | Pavlin | ........................... | 528/272 |
| 7,329,719 B2 * | 2/2008 | Pavlin | ........................... | 528/272 |
| 7,745,546 B2 * | 6/2010 | MacQueen et al. | ........... | 525/408 |
| 2002/0019510 A1 * | 2/2002 | Orth et al. | ...................... | 528/335 |
| 2002/0035237 A1 * | 3/2002 | Lawson et al. | ................ | 528/335 |
| 2002/0037993 A1 * | 3/2002 | Lawson et al. | ................ | 528/335 |
| 2002/0068811 A1 * | 6/2002 | Orth et al. | ...................... | 528/335 |
| 2002/0187170 A1 * | 12/2002 | Pavlin | ........................... | 424/401 |
| 2003/0065084 A1 * | 4/2003 | MacQueen et al. | ........... | 524/538 |
| 2003/0069388 A1 * | 4/2003 | Lawson et al. | ................ | 528/335 |
| 2003/0162938 A1 * | 8/2003 | Pavlin et al. | ................... | 528/310 |
| 2003/0236387 A1 * | 12/2003 | Pavlin | ........................... | 528/272 |
| 2004/0186263 A1 * | 9/2004 | Pavlin | ........................... | 528/232 |
| 2005/0165212 A1 * | 7/2005 | MacQueen et al. | ........... | 528/310 |
| 2005/0197479 A1 * | 9/2005 | Pavlin | ............................. | 528/64 |
| 2005/0267231 A1 * | 12/2005 | Pavlin | ........................... | 523/102 |
| 2006/0052576 A1 * | 3/2006 | Pavlin | ........................... | 528/310 |
| 2006/0204461 A1 * | 9/2006 | Pavlin | ............................. | 424/64 |
| 2007/0244294 A1 * | 10/2007 | Pavlin | ........................... | 528/340 |
| 2009/0076175 A1 * | 3/2009 | Pavlin | ........................ | 514/772.3 |
| 2009/0082460 A1 * | 3/2009 | Pavlin | ........................... | 514/617 |
| 2009/0130041 A1 * | 5/2009 | MacQueen et al. | ............. | 424/64 |
| 2010/0063165 A1 * | 3/2010 | Pavlin | ........................ | 514/772.1 |
| 2010/0166691 A1 * | 7/2010 | Pavlin | ............................. | 424/64 |

OTHER PUBLICATIONS

Perkins, Carol: Lai, Griffin Hydrocarbon-Terminated Polyether-Polyamide Block Copolymers in Personal Car and Other Products IP.COM IPCOM000012564D May 14, 2003.*

* cited by examiner

*Primary Examiner* — James J Seidleck
*Assistant Examiner* — Peter A Salamon

(57) ABSTRACT

Polyether poly(ester-amide) block copolymer having a softening point between 60° C. and 180° C., formed from reaction mixtures comprising a diacid, a poly(alkyleneoxy)diamine, and a poly(alkyleneoxy)polyol, wherein said diacid is a cyclohexane dicarboxylic acid; or formed from reaction mixtures comprising a diacid, a short chain aliphatic diamine having 2-6 carbons, and a poly(alkyleneoxy)polyol. Methods for making and using said block copolymers, compositions and articles comprising said block copolymers.

20 Claims, No Drawings

POLYALKYLENE GLYCOL-BASED POLY(ESTER-AMIDE) POLYMERS, METHODS OF MAKING AND METHODS OF USING SAME, COMPOSITIONS AND PRODUCTS COMPRISING SAME

BACKGROUND OF THE INVENTION

1. Field of the Invention

The present disclosure is directed to polyether poly(ester-amide) block copolymers, methods of making and methods of using such polymers, and compositions and products comprising such polymers. More specifically, the present disclosure is directed to polyalkylene glycol-based poly(ester-amide) (PGPEA) polymers, methods of making and methods of using such polymers, and compositions and products comprising such polymers. The present invention is further directed to the use of such PGPEA polymers as gelling agents, and to compositions comprising PGPEAs wherein the composition is a gel.

2. Description of the Related Art

In many commercially important compositions, the consistency of a product is critical to its commercial success. Examples include personal care, household care, industrial care, and medicated products, which generally contain one or more active ingredients within a carrier formulation. While the active ingredient(s) determine the ultimate performance utility of the product, the carrier formulation is critical to the commercial success of the product in that it largely determines the consistency of the product. The rheology of the carrier or "base" largely determines the manner in which the consumer will apply or use the product. Many commercial and would-be commercial products depend upon the availability of materials called "gelling agents" that have the ability to modify various rheological properties, in order to allow formulation of a successful product.

Products are often desired to be "gels," in that they maintain their shape when undisturbed but flow upon being sheared. Transparent gelled carriers are especially desired by formulators who develop products wherein a colorant is an active ingredient, for example in a lipgloss or rouge, because a transparent carrier (as opposed to an opaque carrier) will minimally, if at all, interfere with the appearance of the colorant. In recent years, consumers have demonstrated an increasing preference for transparent and colorless personal care products such as deodorants and shampoos.

Certain polyamide poly(ester-amide), and polyether-polyamide resins as gellants in formulations for surface-, air-, and personal care are known in the art.

U.S. Pat. No. 3,839,245 to Emery Industries, Inc. discloses a preparation useful as polymer fiber anti-static blend components. The disclosed materials comprise dimer acid as the sole diacid and comprise polyether segment levels of up to 75% by weight of the total polymer.

U.S. Pat. No. 4,230,838 to ATO Chemie discloses block copolymer antistatic compositions comprised of polyether and polyamide blocks arranged linearly and joined together with linking ester groups. The poly(ether-ester-amides) have molecular weights below the fiber-forming range and contain a specified amount of the polyether block and a definite ratio of amide to ester linkages. They are blended with polyesters, polyamides and other fiber-forming polymers to impart antistatic properties. The '838 disclosure does not teach or suggest use of such polymers as gellants (the softening points disclosed in the examples are very high, typically 180° C., making these unsuitable for gellant applications). In addition, the disclosure does not teach or suggest dimer acid- and/or CHDA-based compositions.

U.S. Pat. No. 5,783,657 to Union Camp Corporation (1998), discloses dimer acid-based polyamide compositions which dissolve in non-polar liquids such as mineral oil and, when cooled to room temperature, form firm, transparent gels. The compositions are specific in requiring that they contain an amount of ester groups and, furthermore, that these esters must be located at the ends of the polymer chain.

U.S. Pat. No. 6,111,055, to Union Camp Corporation and Bush Boake Allen (2000), discloses an ester-terminated dimer acid-based polyamide which may be blended with a solvent to form a gel. The solvent may be flammable, and a wick may be added to the resulting gel so as to form a candle. A wick may or may not be present in this gel, but in any event, the composition provides for the release of the fragrance, insecticide or insect-repellent.

U.S. Pat. No. 6,242,509, discloses an ester-terminated dimer acid-based polyamide which may be blended with a solvent to form a gel. The solvent may be flammable, and a wick may be added to the resulting gel so as to form a candle. Depending on the composition, the candle may be formed into a free standing pillar, or may be better suited to being placed in a container. The solvent may be mineral oil. The ester-terminated dimer acid-based polyamide may also be combined with an active ingredient, such as a fragrance, colorant, insect-repellant, insecticide, bioactive ingredient or the like, to afford a delivery vehicle for the active ingredient.

U.S. Pat. No. 6,268,466, (2001) to Arizona Chemical Company, discloses a dimer-acid polyamide which can dissolve in non-polar liquids such as mineral oil and form transparent gets upon cooling. The compositions are specific in requiring that the polymer chains be terminated with tertiary amide groups.

U.S. Pat. No. 6,399,713 to Arizona Chemical Company (2002) discloses polyamide gelling agents (PAOPAs, for poly (alkyleneoxy)-terminated polyamides), consisting of the reaction product of dimer acid, ethylene diamine (EDA), a poly(oxyethylene/propylene)diamine, and a poly(oxyethylene/propylene)monoamine.

U.S. Pat. No. 6,469,131, discloses a block copolymer of the formula hydrocarbon-polyether-polyamide-polyether-hydrocarbon. The copolymer may be prepared by reacting together reactants that include dimer acid, diamine, and a polyether having both hydrocarbon termination and termination selected from one of amine, hydroxyl and carboxyl. The copolymer may be combined with a solvent to form a gel, where the gel may be transparent and may be incorporated into household and consumer products including antiperspirants.

U.S. Pat. No. 6,503,077, discloses a tertiary amide-terminated dimer acid-based polyamide which may be blended with a solvent to form a gel. The solvent may be flammable, and a wick may be added to the resulting gel so as to form a candle. Depending on the composition, the candle may be formed into a free-standing pillar, or may be better suited to being placed in a container. The solvent may, for example, be mineral oil or triglyceride. A solid coating may be placed around the candle, for advantages including to enhance the mechanical stability of the gelled body, and to eliminate the tendency of a gel to have an oily feel and to accept noticeable fingerprints. The solvent which, in combination with the tertiary amine-terminated dimer acid-based polymer forms a gel, may be or include a fragrance material. The gelled composition may also include fatty acid and/or a compound containing one, two, or more ester groups. In one aspect, the article does not contain a wick, and is intended to function as a fragrance-releasing product.

U.S. Pat. No. 6,503,522, discloses a structured, solid composition that contains at least one colorant, a liquid oil phase, and a gellant, wherein the gellant is a tertiary amide-terminated polyamide resin (ATPA) comprising a number of repeating units wherein terminal amide groups constitute from 10% to 50% of the total amide groups.

U.S. Pat. No. 6,552,160, discloses a resin composition prepared by reacting components comprising dibasic acid, diamine, polyol and monoalcohol, wherein (a) at least 50 equivalent percent of the dibasic acid comprises polymerized fatty acid; (b) at least 50 equivalent percent of the diamine comprises ethylene diamine; (c) 10-60 equivalent percent of the total of the hydroxyl and amine equivalents provided by diamine, polyol and monoalcohol are provided by monoalcohol; and (d) no more than 50 equivalent percent of the total of the hydroxyl and amine equivalents provided by diamine, polyol and monoalcohol are provided by polyol. The resin composition may be formulated into, for example, personal care products, fragrance releasing products and candles.

U.S. Pat. No. 6,592,857, discloses a low molecular weight, tertiary amide terminated polyamide which may be blended with a liquid hydrocarbon to form a transparent composition having gel consistency, and this gel may be used to formulate a cosmetic. The tertiary amide terminated polyamide may be prepared by reacting "x" equivalents of dicarboxylic acid wherein at least 50% of those equivalents are from polymerized fatty acid, "y" equivalents of diamine such as ethylene diamine, and "z" equivalents of a monofunctional reactant having a secondary amine group as the only reactive functionality. The gel contains about 5-50% tertiary amide terminated polyamide, with the remainder preferably being pure hydrocarbon.

U.S. Pat. No. 6,864,349, discloses polymerized fatty acid-based polyamides which may be combined with low polarity and high polarity co-solvents to produce homogeneous water-in-oil emulsions. These emulsions are useful in applications favoring an oil base, such as skin creams and cosmetics with emulsions of low stiffness, and car polish with emulsions of greater stiffness.

U.S. Pat. No. 6,875,245, discloses a resin composition prepared by reacting components comprising dibasic acid, diamine, polyol and monoalcohol, wherein (a) at least 50 equivalent percent of the dibasic acid comprises polymerized fatty acid; (b) at least 50 equivalent percent of the diamine comprises ethylene diamine; (c) 10-60 equivalent percent of the total of the hydroxyl and amine equivalents provided by diamine, polyol and monoalcohol are provided by monoalcohol; and (d) no more than 50 equivalent percent of the total of the hydroxyl and amine equivalents provided by diamine, polyol and monoalcohol are provided by polyol. The resin composition may be formulated into, for example, personal care products, fragrance releasing products and candles.

U.S. Pat. No. 6,956,099 to Arizona Chemical Company (2005) discloses polyether polyamide (PEPAs) gelling agents comprising the reaction product of dimer acid, a diamine. The disclosed copolymers have linked internal polyether blocks and internal polyamide blocks and have advantageous physical properties and solvent-gelling abilities. The copolymer may be prepared from a reaction mixture that contains 1,4-cyclohexane dicarboxylic acid (CHDA) and poly(alkyleneoxy) diamine (PAODA). Optionally, the reaction mixture contains no monofunctional compound reactive with either amine or carboxylic acid groups, however some of this monofunctional compound may be present. Dimer diamine and/or dimer acid may be present in the reaction mixture. A copolymer may also be prepared from a reaction mixture containing dimer acid and at least two diamine compound(s) including PAODA and short-chain aliphatic diamine having 2-6 carbons (SDA).

Despite advances in the art, there remains a need for novel polyamide resins capable of functioning as gelling agents. Although references in the art wherein the use of a poly(alkyleneoxy)diamine as a reactive component is stipulated or allowed as optional are known, none of the references disclose or suggest the use of a poly(alkyleneoxy)polyol as a reactive component. The present disclosure is directed to fulfilling these needs and provides additional advantages as described more fully herein.

SUMMARY OF THE INVENTION

The following presents a general summary of some of the many possible embodiments of this disclosure in order to provide a basic understanding of this disclosure. This summary is not an extensive overview of all embodiments of the disclosure. This summary is not intended to identify key or critical elements of the disclosure or to delineate or otherwise limit the scope of the claims. The following summary merely presents some concepts of the disclosure in a general form as a prelude to the more detailed description that follows.

According to one non-limiting embodiment of the present disclosure there is provided a polyether poly(ester-amide) block copolymer. Generally the copolymer is formed from a reaction mixture comprising a diacid, a short chain aliphatic diamine having 2-6 carbons, and a poly(alkyleneoxy) (PAO) polyol. The diacid may be polymerized fatty acid. The polymer may comprise PAO-containing components in the range of about 20-50 wt %. In one embodiment, at least 75% of the dibasic equivalents come from polymerized fatty acid. In another embodiment, about 40% to about 80% of all hydroxyl and amine equivalents come from said short chain diamine. In other embodiments, about 5% to about 55% of all hydroxyl and amine equivalents come from PAO polyol. The PAO polyol may be selected from the group consisting of di-, tri-, tetra-ethylene glycols, di-, tri-, tetra-propylene glycol, di-, tri-, tetra-butylene glycols, and higher molecular weight poly(ethylene glycol)s, poly(propylene glycol)s, poly(butylenes glycol)s, mixed poly(ethyleneoxy-co-propyleneoxy)glycol polymers, and any combination thereof. In even other embodiments, from about 0.1% to 30% of all hydroxyl and amine equivalents come from the monofunctional compound. The monofunctional compound may be selected from the group consisting of PAOMA, PGMO. The reaction mixture for making copolymer of the present disclosure may further comprises one or more monofunctional compound(s) reactive with carboxylic acid or amine groups.

According to even another non-limiting embodiment of the present disclosure there is a composition comprising a polyether poly(ester-amide)polymer and a compound, where the compound is a liquid at room temperature in neat form. Generally the composition is in the form of a gel. In one embodiment, the compound comprises at least one chemical group selected from ester, ether, halogen, carbonate and sulfoxide.

According to another non-limiting embodiment of the present disclosure there is provided a process for preparing a polyether poly(ester-amide)polymer of the disclosure wherein said block copolymer has a softening point between 60° C. and 180° C. and is formed from a reaction mixture comprising a diacid, a short chain aliphatic diamine having 2-6 carbons, and a poly(alkyleneoxy) (PAO) polyol. Generally the process comprises reacting together reactants comprising a diacid, a short chain aliphatic diamine having 2-6 carbons, and a poly(alkyleneoxy)polyol.

According to still another non-limiting embodiment of the present disclosure there is provided a process for preparing a gel comprising combining a copolymer of the disclosure with a compound at elevated temperature to provide a mixture, and allowing the mixture to cool to room temperature to form a gel. Generally the compound is a liquid at room temperature in neat form, and comprises hydroxyl and/or ether functionality.

According to yet another non-limiting embodiment of the present disclosure there is an article comprising a polyether poly(ester-amide) block copolymer of the disclosure. Generally the copolymer has a softening point between 60° C. and 180° C. and is formed from a reaction mixture comprising a diacid, a short chain aliphatic diamine having 2-6 carbons, and a poly(alkyleneoxy) (PAO) polyol. In one embodiment, the article may be formulated as a fragrance stick, an air freshener, a fragrance gel, or a personal care product comprising at least one physiologically acceptable oil. The articles may further comprise a surfactant having an HLB value between 4 and 20. The articles may further comprise at least one of a colorant and a fragrance.

According to even still another non-limiting embodiment of the present disclosure there is provided a polyether poly (ester-amide) block copolymer formed from a reaction mixture comprising a diacid, a poly(alkyleneoxy)diamine, and a poly(alkyleneoxy) (PAO) polyol, wherein said diacid is a cyclohexane dicarboxylic acid. Generally the copolymer has a softening point between 60° C. and 180° C. The reaction mixture may further comprise a co-diacid. The reaction mixture may further comprise one or more monofunctional compound(s) reactive with carboxylic acid or amine groups. In one non-limiting embodiment, the cyclohexane dicarboxylic acid may be 1,4-cyclohexanedicarboxylic acid. In another non-limiting embodiment, the co-diacid may be polymerized fatty acid. In even another non-limiting embodiment, the diamine may exclude diamines of the formula $H_2N-R^2-NH_2$ wherein $R^2$ is $C_2-C_6$ hydrocarbyl. One example of a diamine suitable for use herein is a poly(alkyleneoxy)diamine (PAODA). The PAO polyol may be selected from the group consisting of di-, tri-, tetra-ethylene glycols, di-, tri-, tetra-propylene glycol, di-, tri-, tetra-butylene glycols, and higher molecular weight poly(ethylene glycol)s, poly(propylene glycol)s, poly(butylenes glycol)s, mixed poly(ethyleneoxy-co-propyleneoxy)glycol polymers, and any combination thereof.

According to even yet another non-limiting embodiment of the present disclosure there is provided a process for preparing a block copolymer of the disclosure. Generally the process comprises reacting together reactants comprising a diacid, a poly(alkyleneoxy)diamine, and a poly(alkyleneoxy) polyol, wherein said diacid is a cyclohexane dicarboxylic acid.

According to still even another non-limiting embodiment of the present disclosure there is provided a composition comprising a) a polyether poly(ester-amide) block copolymer of the disclosure and b) a compound, where the compound is a liquid at room temperature in neat form. Generally the composition is in the form of a gel. Generally the copolymer is formed from a reaction mixture comprising a diacid, a poly(alkyleneoxy)diamine, and a poly(alkyleneoxy)polyol, wherein said diacid is a cyclohexane dicarboxylic acid. The compound generally comprises at least one chemical group selected from ester, ether, halogen, carbonate and sulfoxide.

According to still yet another non-limiting embodiment of the present disclosure there is provided a method for preparing a gel, comprising combining a polyether poly(ester-amide) block copolymer of the disclosure with a compound at elevated temperature to form a mixture, and allowing the mixture to cool to room temperature to form the gel. Generally the compound is a liquid at room temperature in neat form, and comprises hydroxyl and/or ether functionality.

According to yet even another non-limiting embodiment of the present disclosure there is provided an article comprising a polyether poly(ester-amide) block copolymer of the disclosure. Generally the copolymer has a softening point between 60° C. and 180° C. and is formed from a reaction mixture comprising a diacid, a poly(alkyleneoxy)diamine, and a poly (alkyleneoxy)polyol, wherein said diacid is a cyclohexane dicarboxylic acid. In one embodiment, the article may be formulated as a fragrance stick, an air freshener, a fragrance gel, or a personal care product comprising at least one physiologically acceptable oil. The articles may further comprise a surfactant having an HLB value between 4 and 20. The articles may further comprise at least one of a colorant and a fragrance.

According to yet still another non-limiting embodiment of the present disclosure there is provided a polyether poly(ester-amide) block copolymer comprising at least one structure selected from the group consisting of structure I, structure II, structure III, structure IV, structure V and structure VI:

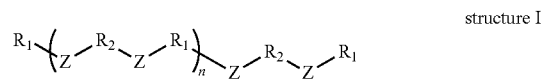

structure I wherein $R_1$=polymerized fatty acid, hydrogenated or non-hydrogenated;
Z=O or NH;
$R_2$=poly(alkyleneoxy) moiety if Z=O,
or $R_2$=2-12 carbon straight chain or branched alkyl moiety if Z=NH; and
n=20, such that the ratio of (—O—$R_2$—O—) to (—NH—$R_2$—NH—) is 3 to 1;

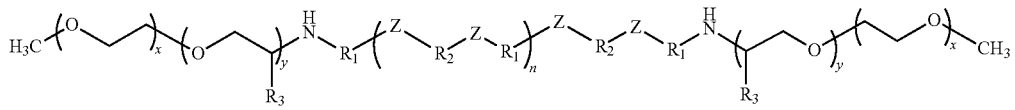

structure II wherein $R_1$=polymerized fatty acid, hydrogenated or non-hydrogenated;
Z=O or NH;
$R_2$=poly(alkyleneoxy) moiety if Z=O;
or $R_2$=2-12 carbon straight chain or branched alkyl moiety if Z=NH;
n=20, such that the ratio of (—O—$R_2$—O—) to (—NH—$R_2$—NH—) is 3 to 1;
x=ethylene oxide (EO) groups;
y=ethylene oxide (EO) groups where $R_3$=H;
or y=propylene oxide (PO) groups where $R_3$=$CH_3$; and
$R_3$=H for (EO), or $CH_3$ for (PO);

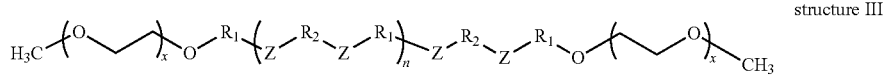

structure III wherein $R_1$=polymerized fatty acid, hydrogenated or non-hydrogenated;
Z=O or NH;
$R_2$=poly(alkyleneoxy) moiety if Z=O;
or $R_2$=2-12 carbon straight chain or branched alkyl moiety if Z=NH;
n=20, such that the ratio of (—O—$R_2$—O—) to (—NH—$R_2$—NH—) is 3 to 1; and x=15;

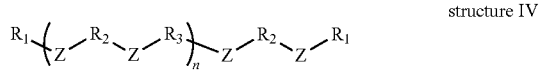

structure IV wherein $R_1$=polymerized fatty acid, hydrogenated or non-hydrogenated;
Z=O or NH;
$R_2$=poly(alkyleneoxy) moiety if Z=O;
or $R_2$=2-12 carbon straight chain or branched alkyl moiety if Z=NH;
$R_3$=polymerized fatty acid, hydrogenated or non-hydrogenated;
or $R_3$=cyclohexane dicarboxylic acid, such that the ratio of polymerized fatty acid to CHDA is 5 to 1 or greater; and
n=20, such that the ratio of (—O—$R_2$—O—) to (—NH—$R_2$—NH—) is 3 to 1;

wherein $R_1$=polymerized fatty acid, hydrogenated or non-hydrogenated;
Z=O or NH;
$R_2$=poly(alkyleneoxy) moiety if Z=O;
or $R_2$=2-12 carbon straight chain or branched alkyl moiety if Z=NH;
$R_3$=polymerized fatty acid, hydrogenated or non-hydrogenated;
or $R_3$=cyclohexane dicarboxylic acid, such that the ratio of polymerized fatty acid to CHDA is 5 to 1 or greater;
n=20, such that the ratio of (—O—$R_2$—O—) to (—NH—$R_2$—NH—) is 3 to 1; and
x=15.

These and other objects of the present disclosure will become apparent to those of skill in the art upon review of this patent specification.

DETAILED DESCRIPTION OF THE INVENTION

The prevent disclosure provides polyether poly(ester-amide) block copolymers, methods of making and methods of using same, and compositions and articles comprising same. More specifically, the prevent disclosure provides polyakylene glycol-based poly(ester-amide) (PGPEA) polymers, methods for making PGPEAs, methods for using PGPEAs, and compositions and articles comprising PGPEAs. The

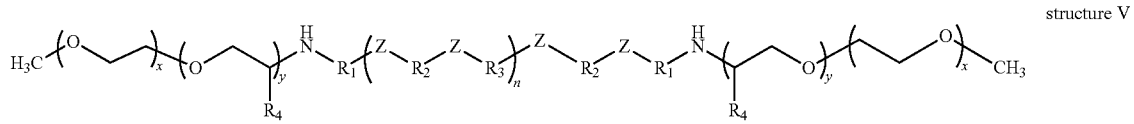

structure V wherein $R_1$=polymerized fatty acid, hydrogenated or non-hydrogenated;
Z=O or NH;
$R_2$=poly(alkyleneoxy) moiety if Z=O;
or $R_2$=2-12 carbon straight chain or branched alkyl moiety if Z=NH;
$R_3$=polymerized fatty acid, hydrogenated or non-hydrogenated; and
or $R_3$=cyclohexane dicarboxylic acid, such that the ratio of polymerized fatty acid to CHDA is 5 to 1 or greater:
n=20, such that the ratio of (—O—$R_2$—O—) to (—NH—$R_2$—NH—) is 3 to 1;
$R_4$=H for (EO), or $CH_3$ for (PO);
x=ethylene oxide (EO) groups;
y=ethylene oxide (EO) groups where $R_4$=H; and
or y=propylene oxide (PO) groups where $R_4$=$CH_3$;

present PGPEA polymers are suitable for use in a variety of applications such as, for example, as gelling agents ("gellants"). The polymers and compositions of the present disclosure may be formulated into any of a variety of products and articles of manufacture. Such products and articles of manufacture include products and articles directed to areas of use including but not limited to surface care, air care, and personal care, and include products such as but not limited to personal care products, medical products, household products, paint strippers, air fresheners, medicament applicators, polishes, and the like which are generally in a gel or thickened state.

Compared to conventional polyamide gellants such as polyalkyeneoxy-terminated polyamides (PAOPAs) and polyether polyamides (PEPAs), the inventive PGPEA polymers are structurally distinct from known polyamide gellants and

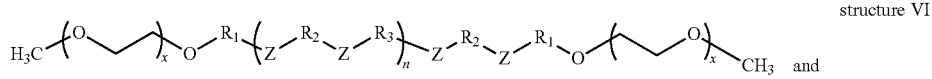

structure VI and comprise a significant level of ester groups within the main chain (backbone). Similar to PAOPAs and PEPAs, the PGPEAs are rich in polyether segments. However, the polyether segments of the PGPEAs originate for the most part from a diol, as opposed to a diamine as is the case for both the PAOPAs and PEPAs. The present diol reactant links the requisite dicarboxylic acids of the PGPEA chain via ester groups instead of amide groups. Because diols are generally less expensive than diamines, the present PGPEA resins generally cost less to produce than the PAOPA or PEPA resins.

The terms "polyalkylene glycol-based poly(ester-amide) polymer" and "PGPEA" and "polyether poly(ester-amide) block copolymer" and "polymer of the disclosure" and "copolymer of the disclosure" and "resins of the disclosure" are all used herein in reference to the inventive polyalkylene glycol-based poly(ester-amide)polymers of the present disclosure. The polymers may also be referred to herein as "gellants of the disclosure" and "gelling agents of the disclosure".

The PGPEA polymers of the present disclosure are the reaction product of: i) one or more diacid, ii) a diamine, and iii) poly(alkyleneoxy)polyol, such as a poly(alkylene glycol). A monofunctional chain terminator may optionally be included in the reaction. Two non-limiting examples of polyols suitable for use herein include poly(ethylene glycol) and poly(propylene glycol). Generally the poly(alkyleneoxy) polyol is used in a relatively larger amount and may be the sole source of polyether block segments of the resulting polymer. The resulting PGPEA polymers are polyether poly(ester-amide) block copolymers.

In one non-limiting embodiment, the present PGPEA polymers comprise a monofunctional chain terminator and are terminated, for example, by PAO-containing monoamines or mono-alcohols. PGPEA resins comprising a monofunctional chain terminator are prepared by reacting together dibasic acid, diamine, poly(alkyleneoxy)polyol, and a monofunctional chain terminator wherein: i) at least 75% of the dibasic acid equivalents come from polymerized fatty acid; ii) from between 40% and 80% of all hydroxyl and amine equivalents come from a short-chained 2-6 carbon atom aliphatic diamine; iii) 5-55% of all hydroxyl and amine equivalents come from poly(alkyleneoxy)polyol; and iv) up to (but no more) than 30% of all hydroxyl and amine equivalents come from the monofunctional chain terminator.

In another non-limiting embodiment, the present PGPEA polymers lack a monofunctional terminator. For example, the inventive PGPEAs may be high enough in molecular weight that the terminal group is of no consequence and thus optional. PGPEA resins lacking a monofunctional terminator are prepared by reacting the dibasic acid, diamine, and poly(alkyleneoxy)polyol components wherein: i) at least 75% of the dibasic acid equivalents come from polymerized fatty acid; ii) from between 40% and 80% of all hydroxyl and amine equivalents come from a short-chained 2-6 carbon atom aliphatic diamine; and iii) 5-55% of all hydroxyl and amine equivalents come from poly(alkyleneoxy)polyol.

Two key requirements for a successful gellant are that it's softening point is in excess of about 60° C. and that it is neither too soluble nor too insoluble in a target liquid so that when it is blended with a liquid, the mixture becomes a solid at a sufficiently low temperature, preferably room temperature. It is known that polyesters, and especially polyesters constructed from poly(alkyleneoxy)polyols, have much lower softening points and much better solubility than the corresponding amides of similar chain structure. Therefore, it is surprising that the present poly(ester-amide)s containing large amounts of alkyleneoxy polyols possess the requisite solidity and solubility to function as gellants.

The polymers of the present disclosure generally have a weight average molecular weight of between 10,000 and 50,000, as measured using gel permeation chromatography with polystyrene as reference standards. In other embodiment, the polymers may have a weight average molecular weight of between 12,000 and 40,000, and in even other embodiments the weight average molecular weight may be between 15,000 and 30,000. The polymers of the present disclosure generally have an amine number and an acid number each of less than 20, in some embodiments each number may be less than 15. The polymers of the present disclosure generally have a softening point between 60° C. and 180° C. In some embodiment, the polymers may have a softening point between 80° C. and 160° C., and in other embodiments the softening point may be between 100° C. and 140° C.

Diacid Reactant

The dibasic acid may be an organic molecule containing at least two carboxylic acid groups or reactive equivalents thereof. In one non-limiting embodiment, the dibasic acid is polymerized fatty acid. The polymerized fatty acid may be a liquid, with an acid number on the order of about 180 to about 200. The polymerized fatty acid may be hydrogenated prior to being used in the resin-forming reaction of the invention. A more detailed discussion of fatty acid polymerization may be found in, e.g., U.S. Pat. No. 3,157,681 and *Naval Stores—Production, Chemistry and Utilization*, D. F. Zinkel and J. Russell (eds.), Pulp. Chem. Assoc. Inc., 1989, Chapter 23, fully incorporated herein by reference.

In addition to polymerized fatty acid, or reactive equivalents thereof, the dibasic acid may comprise co-diacid of the formula HOOC—$R^1$—COOH or reactive equivalents thereof. Co-diacids other than polymerized fatty acid, when present, are preferably used in a minor amount that is, less than 25% of the total amount of diacids on an equivalent basis.

Diamine Reactant

In some non-limiting embodiments of the present disclosure, the diamine reactant may be a short-chained aliphatic diamine. Short-chained aliphatic diamine reactants useful herein may have two primary amine groups and contain from 2-12 carbon atoms. Short-chained aliphatic diamine reactants useful herein may be represented by the formula $H_2N$—$R^2$—$NH_2$ where $R^2$ is a straight-chained or branched alkyl diradical. In one embodiment, the short-chained diamine reactants are selected from the group consisting of ethylene diamine, propylene diamine, methylpentamethylene diamine, hexamethylene diamine, and 1,12-dodecane diamine.

Diamines other than the short chained diamine may be referred to herein as co-diamines. When present, co-diamines are preferably used in a minor amount, that is, less than 50% of the total amount of all amines and alcohols present on an equivalent basis.

In some non-limiting embodiments of the present disclosure, the principal diacid of the PGPEA may be a cyclohexane dicarboxylic acid (CHDA), in which case there is no short chained diamine in the reaction mixture. Thus, in these embodiments wherein the reaction mixture does not contain short chained diamine, the "co-diamine" is actually the only diamine present.

The co-diamine may be cyclic, for example, piperazine or contain oxygen atoms in the form of a polyalkylene oxide group. Exemplary polyalkylene oxide-based co-diamines (PAO diamines) include, without limitation, the JEFFAMINE® diamines, i.e., poly(alkyleneoxy)diamines from Huntsman Chemical (Salt Lake City, Utah), also known as polyether diamines. Preferred polyalkylene oxide-containing co-diamines are the JEFFAMINE® D- and XTJ-series diamines.

Polyol Reactant

The poly(alkyleneoxy)polyol, referred to here as "polyol", may be any ethoxylated or propoxylated polyol, such as polyethoxylated glycerol or polypropoxylated trimethylolpropane. Polyols useful herein have the formula:

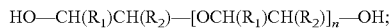

$$HO—CH(R_1)CH(R_2)—[OCH(R_1)CH(R_2)]_n—OH;$$

wherein $R_1$ and $R_2$ are independently selected in each instance from $H_1$, $CH_3$ (methyl), and $CH_2CH_3$ (ethyl). The integer "n" is preferably at least 2 and more preferably >2 such that the glycol molecular weight is from about 200 to about 4,000. Suitable polyols for use in preparing resin of the present invention include di-, tri-, tetra-ethylene glycols, di-, tri-, tetra-propylene glycol, di-, tri-, tetra-butylene glycols, and higher molecular weight poly(ethylene glycol)s, poly(propylene glycol)s, poly(butylenes glycol)s, and mixed poly(ethyleneoxy-co-propyleneoxy)glycol polymers.

Monofunctional Reactant

The monofunctional terminator suitable for use herein may be any monoacid, monoamine, or monoalcohol. In one embodiment, the monofunctional terminator is a poly(alkyleneoxy)monoalcohol or poly(alkyleneoxy)monoamine of the formula:

$$Z—CH(R_1)CH(R_2)—[OCH(R_1)CH(R_2)]_n—OR_3;$$

wherein Z is HO or $H_2N$, $R_1$ and $R_2$ are independently selected in each instance from —H, —$CH_3$, and —$CH_2CH_3$ and $R_3$ in independently selected from $C_1$-$C_{18}$ alkyl and $C_6$-$C_{15}$ aryl. The integer "n" is preferably at least 1 and more preferably >2 such that the terminator molecular weight is from about 100 to about 2,000. In one embodiment, the monofunctional terminator is a monoamine polyether such as JEFFAMINE® M-2070 polyether-amine. In another embodiment, the monofunctional terminator is a monoalcohol polyether such as CARBOWAX® MPEG750 methoxy-terminated poly(ethylene glycol).

The term "monocarboxylic acid" refers to an organic molecule having a single carboxylic acid group, i.e., a single group of the structure —COOH. The term "monoamine" refers to an organic molecule having a single amine group, where the amine group may be a primary or secondary amine. The term "monoalcohol" refers to an organic molecule having a single hydroxyl (—OH) group.

One non-limiting example of a monofunctional reactant is a monocarboxylic acid having the structure R—COOH, wherein R is polyether, alkyl, alkenyl, or alkynyl. Another exemplary monofunctional reactant is a monoamine of the structure R—$NH_2$. As used herein, "alkyl" refers to a hydrocarbyl monovalent radical containing only single bonds, while "alkenyl" and "alkynyl" are hydrocarbyl monovalent radicals containing at least one C=C double bond and one carbon triple bond, respectively. The presence of monocarboxylic acid or monoamine in the reaction mixture serves to inhibit further elongation of the resulting polyamide chains, thereby preventing the molecular weight of the copolymer from becoming too large.

Non-limiting examples of monocarboxylic acids suitable for use herein include, without limitation, short-chain aliphatic carboxylic acids, saturated fatty acids (e.g., wherein R is alkyl) and unsaturated fatty acids (e.g., wherein R is alkenyl or alkynyl). Specific exemplary short-chain aliphatic carboxylic acids include, without limitation, acetic, propionic, and butanoic acids, while exemplary saturated fatty acids include, without limitation, valeric, caproic, caprylic, lauric, mystic, palmitic, stearic, isostearic, arachidic, behenic, lignoceric, cerotic, and montanic acids, and exemplary unsaturated fatty acids include, without limitation, caproleic, palmitoleic, oleic, vaccenic, eladic, brassidic, erucic, and nervonic acids. In various additional aspects of the invention, the monocarboxylic acid is up to about 20 weight percent, more preferably up to about 10 weight percent, and even more preferably up to about 5 weight percent, of the reaction mixture used to form a copolymer of the present invention.

Non-limiting examples of monoalcohols are the monoamines as described above wherein the terminal amine group is replaced with a hydroxyl group, and the monocarboxylic acid groups as described above wherein the terminal carboxylic acid group has been reduced to a primary alcohol group.

When monofunctional reactant is present in a polyamide-forming reaction mixture, the amount of monofunctional reactant may be selected in view of the preferred molecular weight of the product polyamide. The molecular weight decreases as the amount of monofunctional reactant in the reaction mixture increases. In various aspects, the monofunctional reactants contributes, less than 5%, or less than 10%, or less than 15%, or less than 20%, or less than 25%, or less than 30%, or less than 40%, or less than 50% of the total weight of the polyamide-forming reactants in the polyamide-forming reaction mixture.

Reaction Conditions

The present disclosure further provides methods for making PGPEAs. Generally the resins of the present disclosure are prepared in a one-step procedure by charging the reactants (one or more diacid, a diamine, polyol (poly(alkylene glycol), and optional monofunctional terminator (including co-diacid and co-diamine, if present) to a vessel, for example a glass vessel, and heating the reaction mixture smoothly with agitation and under a gentle stream of dry nitrogen to about 200-220° C. Nitrogen flow may be increased to aid in water removal. The reaction flask may be fitted with a thermocouple probe, nitrogen inlet, and magnetic stir bar. The flask may have a vapor outlet leading to a moisture trap and exiting to the back of a fume hood. The flask may be covered with aluminum foil or an insulating fiberglass pad. Because one or more of the reactants may be a solid at room temperature, it may be convenient to combine each of the ingredients at a slightly elevated temperature, and then form a homogenous mixture prior to heating the reaction mixture to a temperature sufficient to cause reaction between the components. Reaction progress may be conveniently monitored by periodically measuring the acid and/or amine number of the product mixture. Generally, water generated during this heating period is condensed and removed. Samples may be taken periodically to monitor the progress of the reaction. After a total of about 10-24 hours at this elevated temperature the reaction mixture may be cooled to about 140-160° C. and poured. Properties, including softening point, acid number, amine number, and molecular weight may then be assayed/measured. Generally, the reactions conditions result in a copolymer having satisfactory acid and amine numbers wherein each number is typically less than 20, though the numbers may each be less than 15 in some embodiments. In other embodiments, the amine number may be less than 10.

As one alternative, the reactants may be metered into the reaction vessel rather than being charged all at once in the beginning of the reaction as described above. Also, the reaction vessel may be jacketed to allow heating by hot oil. The vessel may be equipped with a motor-driven paddle-blade stirrer, and may be preferably configured so that it is capable of being evacuated to a low pressure to assist in water removal. Solvents may be present during the formation of the copolymer, however, because solvents do not become incorporated into the structure of the copolymer, solvents are not included within the term "reaction mixture".

The reaction mixture may comprise a catalyst that accelerates ester and/or amide formation. Thus, mineral acid such as phosphoric acid, or tin salts such as dibutyltin oxide, may be present during the reaction. In addition, it is preferred to remove water from the reaction mixture as it is formed upon amide and ester formation. This may be accomplished by maintaining a vacuum on the reacting mixture.

Generally, it is desired that the stoichiometry of the reactants be controlled during preparation of these resins. It is preferred that the equivalents of carboxylic aid are substantially equal to the combined equivalents of hydroxyl- and amine-functional components.

The PGPEA polymers of the present disclosure may be used as gelling agents, also known as structuring agents, thickeners, rheological modifiers, or thixotropic agents. That is, the combination of a PGPEA polymer of the disclosure with a liquid results in the formation of a gel. For example, in one aspect the polyalkylene glycol-based poly(ester-amide) copolymer is a gelling agent for liquid esters such as methyl soyate, glycol ethers such as dipropylene glycol monomethyl ether, hydroxy-substituted esters such as ethyl lactate. In another aspect, the polyalkylene glycol-based poly(ester-amide)copolymer is a gelling agent for polyesters such as dibutyl adipate. Gelation tests are known in the art and any such tests may be used to assay the present polymers as gellants. One simple gelation test comprises stirring 10 parts of polymer and 90 parts of a liquid over heat to about 100° C. to allow the polymer and liquid to form a mixture. Upon cooling to room temperature, the mixture is carefully observed/evaluated for properties such as firmness and clarity.

The present disclosure further provides compositions comprising PGPEA polymer of the present disclosure and a compound or mixture of compounds, where the compound or mixture of compounds is a liquid at room temperature in neat form. The present compositions may be fluid at elevated temperatures and in the form of a gel at a lower temperature, for example, at room temperature. The compound(s) may comprise a functional group, e.g., an ester, alcohol, aromatic ring, ether, halogen, carbonate and/or sulfoxide. The compositions may comprise any one or more additional component generally referred to as an "active component" which provides or enhances the function of the composition.

The present disclosure further provides compositions wherein the composition is a homogeneous mixture of a resin of the disclosure and a liquid. Generally the present compositions are clear solutions at an elevated temperature, that is a temperature greater than the gel temperature, and a clear or nearly clear gel at a temperature below the gel temperature, most desirably, at ambient temperature. Generally the gels of the present disclosure are firm to soft solids, depending on the concentration of the PGPEA gellant that is dissolved in the liquid. The liquid may be aqueous or anhydrous, high in polarity or low in polarity, depending on the exact composition of the poly(ester-amide) which itself can be made to be compatible with either high-medium- or low polarity liquids. By "liquids" is meant any mixture of substances, including solids dissolved in liquids, such that the composition is fluid at use temperature, commonly, room temperature or about 20-25° C.

In another embodiment of the present disclosure there are provided methods for the preparation of compositions resulting from blending a polyether poly(ester-amide)polymer of the disclosure with a compatible liquid. Generally the compositions of the disclosure are prepared by combining a PGPEA and a liquid at an elevated temperature in the range of from about 90-140° C., until the polymer melts and dissolves completely in the liquid medium. Upon cooling, the cooled mixture (i.e., the composition) generally remains homogeneous. In a preferred embodiment, the inventive composition is a gel. In one embodiment, the cooled mixture remains transparent but may in some cases become translucent, hazy, or creamy-white in appearance.

The polymers of the present disclosure may be combined with moderately polar liquids and in other cases with highly polar organic liquids. In still other cases, polymers of the disclosure may be blended with a mixed blend of a highly polar organic liquid and water. Depending on their exact composition, particularly the nature of the poly(alkyleneoxy) moieties, the present resins may be combined with liquids ranging in polarity from esters and aromatic oils to glycols and aqueous solutions of glycols. The present PGPEA resins are suitable for use in a variety of applications including but not limited to gelling fragrance oils (perfumes, essential oils), emollient oils for cosmetic and personal care formulations (all manner of ester-containing substances), surfactants (also called amphiphilic compounds) for producing water-in-oil and oil-in-water emulsions and dispersions, and solvents for paint stripper formulations.

The liquids suitable for use in the present compositions and gels may be any such liquids known in the art. Useful liquids may range in polarity from esters and aromatic oils to glycols and aqueous solutions of glycols. Non-limiting examples of suitable liquids include fragrance oils, perfumes, essential oils, emollient oils such as those used in cosmetic and/or personal care formulations, amphiphilic compounds (surfactants) for producing water-in-oil and oil-in-water emulsions and dispersions, and solvents for paint stripper formulations.

One non-limiting class of suitable gel-forming liquids is esters including but not limited to 2-ethylhexyl (or "octyl") salicylate, useful in formulating sunscreen products, and benzoate esters including alkyl benzoates and benzyl benzoate. Esters are commonly employed in the cosmetics industry for the formulation of many personal care products. Some are amphiphilic compounds possessing HLB values of from 4-18. Other cosmetic esters include glycerol and propylene glycol esters of fatty acids, including the so-called polyglycerol fatty acid esters and triglycerides.

Another non-limiting class of liquids suitable for use with the present PGPEAs to form gels is ethers including but not limited to glycol ether solvents such as the ethylene glycol or propylene di-n-alkyl ethers and the like and the many ethoxylated linear alcohols and phenols that make up the family of amphiphilic compounds called non-ionic surfactants.

Even another non-limiting class of liquids suitable for use herein for forming compositions and gels of the disclosure is alcohols, such as but not limited to ether-alcohols, ester-alcohols, and polyols such as propylene glycol, diethylene glycol, dipropylene glycol monomethly ether, and polypropylene glycols. These alcohols can be gelled in combination with water.

The present disclosure further provides products and articles comprising a PGPEA polymer, PGPEA composition, or PGPEA gel of the disclosure. The polymers, gels and compositions of the present invention may be formulated into any of a variety of products and articles of manufacture known in the art. Such products and articles of manufacture include products and articles directed to areas of use including but not limited to surface care, air care, and personal care, and include products such as but not limited to personal care products, medical products, household products, paint strippers, air fresheners, medicament applicators, polishes, and the like which are generally in a gel or thickened state. Non-limiting examples include: personal care products such as, but not limited to, cosmetics, mascaras, eye shadow, eyeliner, make-up, lipstick, foundation, make-up removers, bath oils, skin moisturizers, sunscreen in cream and lotion forms, lip balms, waterless hand cleaner, medicated ointments, medicament applicators, water-based gels, water-based emulsions, water-based creams, water-based lotions, ethnic hair products and perfume gels; household products such as, but not limited to, automobile wax/polish, candles, furniture polish, metal cleaners/polishes, household cleaners, paint strippers, insect repellents, insecticides, air fresheners, polishes, and the like which are generally in a gel or thickened state. The polymers, compositions and gels of the present disclosure are also suitable for use in, for example, lubricants, hard surface cleaners, inks, corrosion inhibitors, and other products that may benefit from gel-like character.

The products and articles of the disclosure may further comprise one or more active ingredient. In one non-limiting embodiment, the product may emit or otherwise makes available to its surrounding environment one or more active ingredient. Non-limiting illustrative active ingredients include fragrance materials, insecticides, insect-repellent and bioactive ingredients. In another embodiment, the active ingredient may be active while remaining within the gel. Non-limiting examples of such active ingredients include colorant and sunscreen. Non-limiting examples of such products include but are not limited to air fresheners, fragrance sticks, fragranced soft gels, insect repellents, insecticides, color-delivery compositions, sunscreens and other dermatological compositions, and the like.

Thus, the present invention provides a composition comprising a PGPEA polymer as described herein, and a compound or mixture of compounds, where the compound or mixture is a liquid at room temperature in neat form. This composition will typically be fluid at elevated temperature, and will typically be a gel at room temperature. In one aspect, the compound has a functional group, i.e., the compound is not simply a hydrocarbon. In some embodiments, the functional group is ester, or an ether, or a halogen, or a carbonate, or a sulfoxide. Mixtures that may be gelled may comprise one or any combination of these compounds and functional groups. Specific compounds and class of compounds that may be gelled by the PGPEA copolymers of the invention are described next, however, it should be appreciated that the copolymers described herein are capable of gelling a wide range of organic liquids and blends of organic liquids.

In one embodiment, the organic liquids suitable for gelation by the present PGPEA polymers are polar in nature. As used herein, "organic" refers to a chemical component containing at least one carbon atom. A polar liquid is one exhibiting dominant structural moieties of induced positive and negative charge (e.g., methanol), while a nonpolar liquid is one wherein the molecular structure is devoid of regions having induced positive and negative charge (e.g., carbon tetrachloride). Exemplary organic liquids suitable for gelation by the copolymers of the present invention include, without limitation, alcohols such as ethanol and propylene glycol; stripping solvents such as dimethyl sulfoxide (i.e., DMSO), N-methylpyrrolidinone (i.e., NMP), various terpenes and various ketones; epoxies such as EPON.™. 828 (Resolution Performance Products, Houston, Tex.); and polymerizable monomers including alkyl acrylates, polyacrylates and styrene resin solutions.

Ester-containing compounds are another class of liquids suitable for gelation by the copolymers of the present invention. An ester-containing compound will include the structural formula —C(=O)O—, and preferably includes the structural formula —C(=O)—O—R.sup.6 where R.sup.6 is selected from $C_{1-22}$ hydrocarby groups. Such esters may be monofunctional esters (i.e., have a single ester moiety) or may be polyfunctional (i.e., have more than one ester group). Suitable esters include, but are not limited to, the reaction products of $C_{1-24}$ monoalcohols with $C_{1-22}$ monocarboxylic acids, where the carbon atoms may be arranged in a linear, branched and/or cyclic fashion, and unsaturation may optionally be present between carbon atoms. Preferably, the ester has at least about 18 carbon atoms. Examples include, but are not limited to, fatty acid esters such as methyl oleate, methyl linoleate and mixtures containing methyl oleate and methyl linoleate such as methyl soyate or other vegetable oil methyl esters, isopropyl isostearate, n-propyl myristate, isopropyl myristate, n-propyl palmitate and isopropyl palmitate. Other suitable esters include alkyl benzoates such as FINSOLV.™. EB and FINNSOL.™. TN, alkyl salicylates such as methyl salicylate (also known as oil of wintergreen), phthalates such as dioctyl phthalate, glycerol and propylene glycol esters of fatty acids, such as the so-called polyglycerol fatty acid esters (e.g., esters suitable for use in cosmetic formulations, such as glyceryl monostearate) and triglycerides.

Poly(alkyleneoxy)ethers are another class of liquids suitable for gelation by the copolymers of the present invention. Suitable poly(alkyleneoxy)ethers include, without limitation, polyethylene glycol; polypropylene glycol; DOWANOL.™. EPH ethylene glycol monophenyl ether and DOWANOL.™. DPM dipropylene glycol monomethyl ether (available from Dow Chemical, Midland, Mich. USA); surfactants such as TERGITOL.™. NP-4 and TRITON.™. X-100 (both available from Union Carbide), SURFONIC.™. 40, SURFONIC.™. DNP-100, and SURFONIC.™. N60 (all available from Huntsman Chemicals, Houston, Tex.), and polyoxyethylene monolaurate (marketed as GLYCOSPERSE.™. L20 by Lonza, Inc., Fair Lawn, N.J.). Especially suitable are surfactants useful in preparing cosmetics and having an HLB number greater than 4 and less than 20, preferably 6-16. Such surfactants are well known in the art.

In one embodiment the active ingredient may be a fragrance material. Suitable fragrance materials include fine perfumes and commodity fragrance materials. Because almost all fragrance materials are at least moderately polar organic liquids, having functional groups such as alcohols, ethers, ketones and esters, a large number of suitable fragrance materials known to one of ordinary skill in the art may be gelled by the copolymers of the present invention. The fragrance-containing compositions of the present invention provide for controlling the shape and release of fragrance, i.e., providing the fragrance in the form of a solid gel with a steady release of fragrance which lasts for a long time. When the fragrance material is a fine fragrance, the gelled composition is preferably in the form of a stick, which can be rubbed onto a surface to provide a layer of fragrance-releasing material. Such a composition will be referred to herein as a fragrance stick. Alternatively, the gelled composition may be a "soft gel" by which is meant a composition of gelatin-like consistency. A soft gel does not typically hold its structure under stress, and thus is preferably contained within a jar or the like. A soft gel may be applied to the skin or other surface by immersing a finger into the gel and then rubbing the residue from the finger onto another area of the skin. The term "fine fragrance" generally refers to fragrances that are used in fine (e.g., expensive) perfumes. Alternatively, the gelled composition may be an attractively or usefully shaped object that holds its shape or shrinks slightly while the fragrance is released. Such as composition will be referred to herein as an air freshener since it is useful in fragrancing or "freshening" a room, closet, automobile or other enclosed space.

In a typical fragranced stick, air freshener or soft gel of the invention, the fine fragrance is present at a concentration within the range of about 1-70 wt. % of the composition, and preferably constitutes about 2-25 wt. % of the composition. The copolymer is typically present at a concentration within the range of about 5-50 wt. % of the composition, and is preferably present within the range of about 10-20 wt. %. Greater or lesser amounts of these ingredients may be present, depending on the desired consistency of the stick and the compatibility of the fragrance with the copolymer. In general, the gel structure becomes firmer as the concentration of polyether poly(ester-amide) block copolymer increases in the fragrance stick, air freshener, or soft gel and all of these can adopt a "stick" type consistency, which refers to a very firm, even free-standing, gel. The combination of polyether poly(ester-amide) block copolymer and fragrance can afford a clear or transparent structure. Such a transparent structure may increase the aesthetic appeal and application areas of the stick, freshener and gel in the marketplace.

The above articles of this invention are prepared from components that include a PGPEA polymer as described herein. A typical inventive air freshener, fragrance stick or fragrance gel contains polyether poly(ester-amide)copolymer in a concentration range of about 5-60 wt. %, and fragrance in a concentration range of about 1-70, where these weight percent values are based on the total weight of the article. The amounts of polyether poly(ester-amide)copolymer and fragrance present in the air freshener can be varied outside these typical ranges, and still provide a useful product. The precise amounts of polyether poly(ester-amide)copolymer and fragrance to be used in preparing an article will depend on the qualities of the particular polyether poly(ester-amide)copolymer. Typically, a high fragrance content is desirable in, for example, an air freshener because such an air freshener may potentially have a longer useful lifetime. It is usually advantageous to include a colorant, typically a dye, in the article to present an attractive appearance. Colorant levels are typically low on a weight basis, in the range of 0.05% to 2%.

Another active ingredient that may be incorporated into a gel and/or product of the invention is an anti-insect chemical. The term "anti-insect chemical" is intended to encompass materials that are toxic, repugnant or attractive to an insect. The gel containing the anti-insect chemical preferably has the consistency of a stick, or at least a firm gel, and will be referred to herein for convenience as an insect stick. The insect stick of the invention may be used to impart an anti-insect residue, in the form of a thin film, to a surface. Such a residue may be placed onto the surface of a cupboard, for example, in order to kill and/or repel insects from the cupboard. Alternatively, the thin film may be applied to the skin, to repel insects such as mosquitoes from the skin.

In a typical insect stick of the invention, the polyether poly(ester-amide)copolymer content will range from about 5-60 wt. % of the stick, and preferably ranges from about 10-50 wt. %. The content of anti-insect chemical will typically range from 0.1-30 wt. %. The amount of anti-insect chemical to be used in the insect stick will depend on the potency of the anti-insect chemical, as well as its compatibility with the polyether poly(ester-amide)copolymer. Suitable anti-insect chemicals include boric acid, synthetic pyrethroid, D-empenthrin and DEET. Other anti-insect chemicals as known in the art may also or alternatively be incorporated into the gel of the invention. One such chemical is referred to as a pheromone. Such a material can influence the behavior of an insect and thus be used to control its population. A pheromone can, for example, attract an insect to an area where it causes no damage or can be trapped.

The following is a list of chemicals that may be included in a formulation containing polyether poly(ester-amide)copolymer of the present invention, where release of the chemical into the environment will affect the behavior of insects: E or Z-13-octadecenyl acetate, E or Z-11-hexadecenal; E or Z-9-hexadecenal; hexadecanal; E or Z-11 hexadecenyl acetate; E or Z-9-hexadecenyl acetate; E or Z-11-tetradecenal; E or Z-9-tetradecenal; tetradecanal; E or Z-11-tetradecenyl acetate; E or Z-9-tetradecenyl acetate; E or Z-7-tetradecenyl acetate; E or Z-5-tetradecenyl acetate; E or Z-4-tridecenyl acetate; E or Z-9-dodecenyl acetate; E or Z-8 dodecenyl acetate; E or Z-5-dodecenyl acetate; dodecenyl acetate; 11-dodecenyl acetate; dodecyl acetate; E or Z-7-decenyl acetate; E or Z-5-decenyl acetate; E or Z-3-decenyl acetate; Z or E, Z or E 3,13-octadecadienyl acetate; Z or E, Z or E 2,13-octadecdienyl acetate; Z, Z or E-7,11-hexadecadienyl acetate; Z, E 9,12-tetradecadienyl acetate; E, E-8,10-dodecadienyl acetate; Z, E 6,8-heneicosadien-11-one; E, E 7,9-heneicosadien-11-one; Z-6-henicosen-11-one; 7,8-epoxy-2-methyloctadecane; 2-methyl-7-octadecene, 7,8-epoxyoctadecane, Z,Z,Z-1,3,6,9-nonadecatetraene; 5,11-dimethylheptadecane; 2,5-dimethylheptadecane; 6-ethyl-2,3-dihydro-2-methyl-4H-pyran-4-one; methyl jasmonate; alpha-pinene; beta-pinene; terpinolene; limonene; 3-carene; p-cymene; heptane; ethyl crotonate; myrcene; camphene; camphor; cineol; alpha-cubebene; allyl anisole; undecanal; nonanal; heptanal; E-2-hexenal; E-3-hexenal; hexanal; verbenene; verbenone; verbenol; 3-methyl-2-cyclohexenone; 3-methyl-3-cyclohexenone; frontalin; exo and endo brevicomin; lineatin; multistriatin; chalcogran; 7-methyl-1,6-dioxaspiro(4,5-decane, 4,8-dimethyl-4(E), 8(E)-decadienolide; 11-methyl-3(Z)-undecenolide; Z-3-dodecen-11-olide; Z,Z-3,6-dodecen-11-olide; Z-5-tetradecen-13-olide; Z,Z-5,8-tetradecen-13-olide; Z-14-methyl-8-hexadecenal; 4,8-dimethyldecanal; gamma-caprolactone; hexyl acetate; E-2-hexenyl acetate; butyl-2-methylbutanoate; propylhexanoate; hexylpropanoate; butylhexanoate; hexylbutanoate; butyl butyrate; E-crotylbutyrate; Z-9-tricosene; methyl eugenol; alpha-ionone-4-(p-hydroxyphenyl)-2-butanone acetate; E-beta-farnasene; nepetalactone; 3-methyl-6-isopropenyl-9-decenyl acetate; Z-3-methyl-6-isopropenyl-3,9-decadienyl acetate; E or Z-3,7-dimethyl-2,7-octadecadienyl propionate; 2,6-dimethyl-1,5-heptadien-3-ol acetate; Z-2,2-dimethyl-3-isopropenylcyclobutanemethanol acetate; E-6-isopropyl-3,9-dimethyl-5,8-decadienyl acetate; Z-5-(1-decenyl)dihydro-2(3H)-furanone; 2-phenethylpropionate; 3-methylene-7-methyl-7-octenyl propionate; 3,11-dimethyl-2-nonacosanone; 8-methylene-5-(1-methylethyl)spiro(11-oxabicyclo)8.1.0-undecene-2,2-oxira-n-3-one; 2-propylthietane; 3-propyl-1,2-dithiolane; 3,3-dimethyl-1,2-dithiolane; 2,2-dimethylthietane; E or Z-2,4,5-trimethylthiazoline; 2-sec-butyl-2-thiazoline; and isopentenyl methyl sulfide. Specific pheromones include the following: 8-methyl-2-decyl-propionate; 14-methyl-1-octadecene; 9-tricosense; tridecenyl acetate; dodecyl acetate; dodecenyl acetate; tetradecenyl acetate; tetradecadienyl acetate; hexadecenyl acetate; hexadecadienyl acetate; hexadecatrienyl acetate; octadecenyl acetate; dodecadienyl acetate; octadecadienyl acetate; Z,E-9,12-tetradecadiene-1-ol; hexadecenal; octadecenal; acetophenone; amyl acetate; isoamyl acetate; vanillin; or a flavorant selected from coffee, fennel and cinnamon flavor.

Other active ingredients that may be included in an article of manufacture of the present invention functions primarily while being maintained within the gel. Examples of such active ingredients include colorant and sunscreen. When the active ingredient is a colorant, then the product may be used to impart desired coloration to a surface, and/or to hide underlying and undesirable coloration. The active agent may be a sunscreen, where suitable sunscreens include, without limitation, PABA, ethylhexyl p-methoxycinnamate, oxybenzone, 2-ethylhexyl salicylate, octylsalicylate, and metal oxide such as zinc oxide and titanium oxide. The zinc oxide and titanium oxide scatter light so that less light hits the underlying skin.

Another active ingredient that may be included in an article of manufacture of the present invention is a bioactive compound. As used herein, a bioactive compound acts on a biological system to produce a desirable result. In a preferred embodiment, the bioactive compound may be applied to the skin of a person, to have a desirable effect on the person. The gel of the present invention thus can serve as a carrier for delivering the bioactive compound to the biological system, and/or as a means to hold the bioactive compound at a site to which it has been delivered, and/or as a repository of bioactive compound which provides for the controlled release of the bioactive compound to the system. The amount of this type of active ingredient to incorporate into the composition will depend on the desired effect, and such an amount can be readily determined by one of ordinary skill in the art without undue experimentation. At a minimum, the amount should be an effective amount Typically, 0.1-25 wt. %, and more typically 0.5-10 wt % of the active ingredient is sufficient, where the wt. % value is based on the entire weight of the composition.

The bioactive compound may be cosmetic/dermatological agent that produces a desirable result on the host when applied to the host's skin. Exemplary desirable results include, without limitation, anti-fungal activity, hemorrhoid treatment, anti-itching treatment, wart removal or reduction, antibiotic activity, anti-wrinkling, and analgesic effects. Suitable cosmetic/dermatological agents include, without limitation, acetylsalicylic acid, acyclovir, 6-[3-(1-adamantyl)-4-methoxyphenyl]-2-naphthoic acid, amphotericin B, ascorbic acid, benzoyl peroxide, betamethasone valerate, chloroxylenol, citric acid, clindamycin phosphate, clobetasol propionate, clotrimazole, cyproheptadine, diclofenac, diphenylhydramine hydrochloride, econazole, erythromycin, estradiol, glycolic acid, glycyrrhetinic acid, hydrocortisone, hydroquinone, ibuprofen, ketoconazole, kojic acid, lactic acid, lidocaine hydrochloride, metronidazole, miconazole, miconazole nitrate, octopirox, 5-n-octanoylsalicylic acid, paracetamol, pramoxine hydrochloride, progesterone, retinoic acid, retinol, salicylic acid, superoxide dismutases, terbinafine, thenaldine, tocopherol, tolnaftate, trimeprazine, 1,8,10-tripropionyl-9-anthrone, undecylenate, and vitamin D.

The bioactive agent may be function as a topical analgesic, where exemplary topical analgesics include, without limitation, camphor, capsicin, menthol, methyl salicylate, and trolamine salicylate. The bioactive agent may function as an anti-fungal agent, where exemplary anti-fungal agents include, without limitation, clotrimazole, miconazole nitrate, tolnaftate, and undecylenate. Exemplary anti-itching agents include, without limitation, pramoxine hydrochloride and diphenylhydramine hydrochloride. An exemplary anti-wart compound for including in a gel of the invention is salicylic acid. An exemplary hemorrhoid treating compound for including in a gel of the invention is hydrocortisone. An exemplary antibiotic compound for including in a gel of the invention is chloroxylenol.

The bioactive agent may function as a wound-healing aid for preventing and reducing injury to mammalian cells and increasing the resuscitation rate of injured mammalian cells, where an exemplary wound-healing aid is a combination of (a) pyruvic acid and pharmaceutically acceptable salts thereof, and (b) a mixture of saturated and unsaturated fatty acids required for the repair of cellular membranes and resuscitation of mammalian cells. The bioactive agent may be an antioxidant, which inhibits oxidation or suppression reactions promoted by oxygen or peroxides, where exemplary antioxidants include, without limitation, vitamin A, vitamin E, and derivatives thereof. The bioactive agent may function as an anti-acne agent. Exemplary anti-acne agents include, without limitation, benzoyl peroxide and vitamin A acid.

The amount of bioactive ingredient to incorporate into the gel of the invention will depend upon the efficacy of the bioactive ingredient and the desired effect. This amount can be determined by one of ordinary skill in the art without undue experimentation. At a minimum, the amount should be an effective amount. Typically, 0.1 wt % to 25 wt %, and more typically 0.2 wt % to 10 wt % of bioactive ingredient is sufficient.

The article of manufacture containing a PGPEA copolymer of the present invention may be a personal care product, where exemplary personal care products include, without limitation, eye make-up (mascara, shadow), finger nail polish, facial scrubs, lipstick, foundation make-up, costume make-up, as well as baby oil, make-up removers, bath oil, skin moisturizers, sun care products, lip balm, waterless hand cleaner, medicated ointments, ethnic hair care products, perfume, cologne, and suppositories.

The copolymers of the present invention, designated separately, herein as Polymer Class I (dimer diacid) and Polymer Class II (dimer-CHDA diacid combination), may be used to prepare water-based gels, emulsions, creams, and/or lotions. These formulations generally comprise at least one copolymer of the present invention blended with water and a water-soluble polar organic liquid (POL). Examples of suitable POLs include ethylene, propylene and butylenes glycols, lower alcohols and polyglycol alkyl ethers, such as DOWANOL DPM and PROGLYDE DMM. The copolymers of the present invention may be used at a suitable loading, for example 10%, to provide effective gels. The results will vary depending on the ratio of POL/water and the percent of water in the blend. Details of the preparation of such compositions, and the use of such compositions, may be found in Document No. IPCOM000168883-D, accessed at www.ip.com where the copolymers of the present invention may be used in lieu of, or in combination with, the gellants disclosed in the referenced document.

In addition, the polyether poly(ester-amide)copolymer-containing gels of the present invention may be used in household products such as automobile wax/polish, candles, furniture polish, metal cleaners/polishes, household cleaners, paint strippers and insecticide carriers.

The polyether poly(ester-amide)copolymer-containing gels of the present invention may also be used in industrial products such as fuels (sterno, lighter, fire-starters), toilet bowl rings, lubricants/greases, wire rope lubricant, joint and cable fillers, soldering flux, buffing compounds, crayons and markers, modeling clay, rust preventatives, printing inks, paints, protective/removable coatings, and jet inks.

Formulations to prepare such materials are well known in the art. For example, U.S. Pat. Nos. 3,615,289 and 3,645,705 describe the formulation of candles. U.S. Pat. Nos. 3,148,125 and 5,538,718 describe the formulation of lipstick and other cosmetic sticks. U.S. Pat. Nos. 4,275,054, 4,937,069, 5,069,897, 5,102,656 and 5,500,209 each describe the formulation of deodorant and/or antiperspirant.

The gels of the present invention containing an active ingredient may additionally contain optional ingredients. The optional ingredients may serve one or more purposes, such as to facilitate the formation of a homogeneous gel, enhance the delivery properties of the product increase the aesthetic appeal of the product, enhance the ability of the product to release active ingredient, etc.

One suitable optional ingredient is a colorant. The addition of colorant to a gel which will be applied to skin or other surface will provide a marker so that the residue of the gel will be visible on the surface. A preferred fragranced stick or gel, absent the colorant, is clear and transparent, although the fragranced stick or soft gel of the present invention may be opaque or translucent. In any event, the addition of colorant may enhance the visual appeal of the fragranced stick or gel, and the residue provided when the stick or gel is rubbed across a surface. The colorant may be a dye or a pigment, and is preferably non-irritating to the skin when the gel will be applied to skin. Such colorants are well known in the art, and are used in, for example, cosmetics such as lipstick and eye shadow.

When present, the colorant is typically needed in only small amounts, for example, less than 5 wt. %, and often as little of 1 wt. % or even 0.1 wt. % is sufficient to impart a desired coloration to the gel. If a more intense coloration is desired, then the amount of colorant in the gel may be increased. When coloration is desired, the colorant should be present in an amount effective to provide the desired coloration.

Other optional components may serve to enhance the processing of the gel with the active ingredient. For example, the optional component may facilitate formation of a homogeneous mixture between the polyether poly(ester-amide)copolymer gellant and the active ingredient. In addition, the optional component will typically influence the consistency of the gel, and can be used to impart enhanced delivery properties to the stick or gel. For instance, in some cases the incorporation of volatile hydrocarbon or alcohol may enhance the homogeneity of the gel-active ingredient combination, as well as promote the delivery of a thin layer of gel to the skin, with the absence of a concomitant wet residue that might otherwise be present.

The copolymers of the present invention may be used to prepare gelled compositions useful as waxes and polishes, and the present invention provides a method of imparting a shiny appearance to a substrate using a copolymer of the present invention. Details of the preparation of such compositions, and the use of such compositions, are found in Document No. IPCOM000009045-D, accessed through www.ip.com, where the copolymers of the present invention may be used in lieu of, or in combination with, the gellants disclosed in this document. Basically, by utilizing a gellant component, wax and polish compositions which impart outstanding gloss, outstanding mar- and water-resistance, and minimal dirt pick-up to applied substrates can be prepared using the copolymers of the present invention. These compositions exhibit adhesion to polyurethane top-coats common in today's automotive finish market. Surprisingly, compositions exhibiting these properties can be generated very simply, requiring a formulation containing a few as 2 or 3 components, and nothing other than heat and a simple stirring motor to assemble a composition that is homogeneous in appearance, and gel-like, cream-like or paste-like in consistency. thus, these compositions are easy to manufacture and make excellent waxes and polishes for furniture, automobiles, and other substrates. The wax and polish compositions contain gellant, solvent that is gelled by the gellant, and optional ingredients. These compositions are preferably homogeneous in appearance, cream-like, gel-like or paste-like in consistency, and easily applied to substrate surfaces. A paste form of the composition may include an aliphatic solvent, while an emulsion form of the composition may be prepared for liquid/cream applications. The gellants preferably have a non-crystalline structure (transparent) for excellent film formation and even (smooth) surface generation for high gloss development. UV stable and non-UV stable systems can be used for intermediate to long-lasting film integrity. The copolymer imbues the compositions with good hydrolytic stability at extreme ambient temperature and humidity. The waxes can demonstrate excellent water beading/repellency.

The compolymers of the present invention may be used to prepared gelled compositions useful as fire lighting fluids, and the present invention both provides such gelled compositions and provides methods of using such compositions as fire lighting fluids. Details of the preparation of such compositions, and the use of such compositions, are found in Document No. IPCOM000010393D, accessed at www.ip.com, where the copolymers of the present invention may be used in lieu of, or in combination with, the gellants disclosed in this document. Fire lighter fluids can be very efficient means of starting a fire. The low viscosity of these fluids can, however, impede a practical and safe usage. Gelation of these fluids is an elegant way to overcome these disadvantages. Currently such systems already exist for ethanol based systems and are highly successful. However, the low flash point of ethanol is still a point of concern, both in production as in application at the consumer level. The present invention provides for generating a gelled fire lighter system based on mineral oils and other fuels with a much higher and therefore safer flashpoint using the copolymer gelling agents of the present invention.

The copolymers of the present invention may be used to prepare gelled fiber reinforced plastic and gel coats. Details of the preparation of such compositions, and the use of such compositions, are found in Document No. IPCOM000007401D, accessed at www.ip.com, where the copolymers of the present invention may be used in lieu of, or in combination with, the gellants disclosed in this document. Gelled matrix liquid compositions suitable for constructing fiber reinforced plastics and gel coats are hereby provided which comprise a matrix liquid and a copolymer of the present invention, the liquid being a mixture of one or more polymerizable monomers, an unsaturated polyester resin, a curing catalyst and optional components such solvent and inert filler and an organic polyamide gellant. The copolymer of the present invention is readily incorporated into the matrix liquid composition by mild heating and or high shear mixing to form, when cooled, a homogenous, shear-thinnable gel with thixotropic character that prevents separation of the liquid from the fiber matrix or sagging of the gel coat.

The copolymers of the present invention may be used to prepare gelled compositions useful for removing coatings from coated surfaces. Details of the preparation of such compositions, and the use of such compositions, are found in Document No. IPCOM000005738D, accessed at www.ip.com, where the copolymers of the present invention may be used in lieu of, or in combination with, the gellants disclosed in this document. Simply stated, organic coatings may be removed from their substrates by treating the coated substrate with a gelled organic solvent, where the gellant is, or includes, the copolymer of the present invention. For example, paint may be stripped from metal, wood, etc. by the process of contacting the paint with a gelled composition formed from turpentine or other organic solvent in combination with the copolymer of the present invention. The coating dissolves into the gel and/or the solvent from the gel is able to diffuse between the coating and the underlying substrate, thereby dissolving and/or loosening the coating so that the process of removing the gel also removes some or all of the coating. Multiple applications of gelled organic solvent may be needed to completely remove the coating. A gel is particularly advantageous when the coated surface is vertically positioned because the gel will resist running down the coated surface, and accordingly the gel will retain contact with the surface for as long as desired.

The articles of manufacture of the invention may be prepared by combining a PGPEA polymer as described herein with a suitable liquid and heating these materials with stirring until a uniform mixture results. Upon cooling, the mixture will assume a gel or stick-like consistency. One or more active ingredient(s) may also be included and present in the mixture.

Non-limiting embodiments of the disclosure are illustrated in the following examples. In the following examples, chemicals were of reagent grade unless noted otherwise, and were obtained from commercial supply houses.

EXAMPLES

Example 1

Design of PGPEA Polymers

The present PGPEAs may be divided into classes and types (sub-classes) according to the reaction components, and are generally distinct from one another based on the form of the terminal group. Table I lists non-limiting examples of components from which the present PGPEAs may be manufactured.

The present PGPEAs have been divided herein into non-limiting classes and types (sub-classes) as follows: 1) Class I PGPEAs are those based on dimer acid; and 2) Class II PGPEA polymers are those based on CHDA.

With respect to Class I PGPEAs, these generally require EDA as a component. The EDA may be necessary in order to achieve the target softening point. Non-limiting examples of different types of Class I PGPEAs include:

Class I, Type A. Dimer, EDA+PGDO, no specific terminator

Class I, Type B. Dimer, EDA+PGDO, terminated by a PAOMA

Class I, Type C. Dimer, EDA+PGDO, terminated by a PGMO

Of course, it should be clear to one of skill in the art that additional PGPEA classes and types may be created by adding additional components. For example, it should be clear to one of skill in the art, that if it is established that a certain polymer containing, for example, (dimer+EDA+PGDO) is a useful gellant and a polymer made from, for example, (dimer+EDA+PAODA) is a good gellant, then any mixture of these components, that is (dimer+EDA+PGDO+PAODA) may also produce a useful gellant.

Class I, Type A. Dimer, EDA+PGDO, No Specific Terminator
(Polyalkylene Glycol based Polyesteramide (PGPEA))

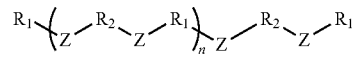

where:
$R_1$=polymerized fatty acid, hydrogenated or non-hydrogenated;
Z=O or NH;
$R_2$=poly(alkyleneoxy)moiety if Z=O,
or $R_2$=2-12 carbon straight chain or branched alkyl moiety if Z=NH; and
n=20, such that the ratio of (—O—$R_2$—O—) to (—NH—$R_2$—NH—) is 3 to 1

Class I Type B. Dimer, EDA+PGDO, Terminated by a PAOMA
(PAOMA Terminated PGPEA (PAOMATPGPEA))

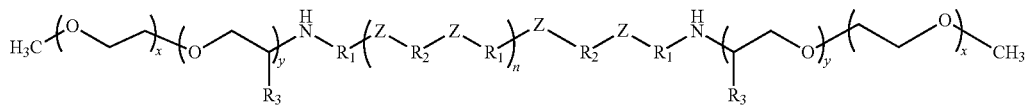

As categorized herein, the Class II PGPEA polymers are those based on CHDA. Generally the Class II PGPEAs will not contain EDA due to the fact that most lower diamines form salts with CHDA which in turn make the reaction mixture intractable. Such a reaction runs only if their use level is very low (<0.5%), in which case the resulting polymer possesses a prohibitively high softening point.

Generally in order to obtain the desired softening point range, Class II PGPEAs are based on PAODA, such as, for example, JEFFAMINE D-400. Such polymers do not require dimer acid in the structure, but its presence lowers the softening point and increases the resin's hydrophobic character thus affecting gelation performance. Dimer acid, then, is a useful, though optional, component. Non-limiting examples of Class II PGPEA types are as follows:

Class II, Type A. CHDA (+dimer), PAODA+PGDO, no specific terminator

Class II, Type B. CHDA (+dimer), PAODA+PGDO, term'd by PAOMA

Class II, Type C. CHDA (+dimer), PAODA+PGDO, term'd by PGMO

Previous work by the present inventor revealed a generally positive effect on gelation performance as a result of increasing the PAO content of a polymer. Thus, in the present examples, PGPEAs having at least 25 wt % and perhaps up to 50 wt % PAO-containing components (for example, PGDO and PGMO) were targeted and analyzed.

Provided below are structures for each of the non-limiting examples of non-limiting Class I and II PGPEAs listed above. As used herein, the term "PGPEA" refers to all classes and types of copolymers of the present invention.

where:
$R_1$=polymerized fatty acid, hydrogenated or non-hydrogenated;
Z=O or NH;
$R_2$=poly(alkyleneoxy)moiety if Z=O;
or $R_2$=2-12 carbon straight chain or branched alkyl moiety if Z=NH;
n=20, such that the ratio of (—O—$R_2$—O—) to (—NH—$R_2$—NH—) is 3 to 1;
x=ethylene oxide (EO) groups;
y=ethylene oxide (EO) groups where $R_3$=H;
or y=propylene oxide (PO) groups where $R_3$=$CH_3$; and
$R_3$=H for (EO), or $CH_3$ for (PO)

Class I, Type C. Dimer, EDA+PGDO, Terminated by a PGMO
(PGMO Terminated PGPEA (PGMOTPGPEA))

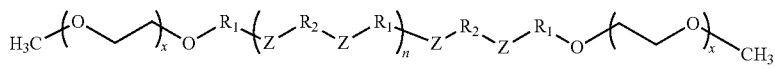

where:
$R_1$=polymerized fatty acid, hydrogenated or non-hydrogenated;
Z=O or NH;
$R_2$=poly(alkyleneoxy)moiety if Z=O;
or $R_2$=2-12 carbon straight chain or branched alkyl moiety if Z=NH;
n=20, such that the ratio of (—O—$R_2$—O—) to (—NH—$R_2$—NH—) is 3 to 1; and
x=15

Class II, Type A. CHDA (+ dimer). PAODA+PGDO. No Specific Terminator
(Polyalkylene Glycol Based Polyesteramide (PGPEA) with CHDA)

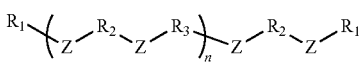

where:
R₁=polymerized fatty acid, hydrogenated or non-hydrogenated;
Z=O or NH;
R₂=poly(alkyleneoxy)moiety if Z=O;
or R₂=2-12 carbon straight chain or branched alkyl moiety if Z=NH;
R₃=polymerized fatty acid, hydrogenated or non-hydrogenated;
or R₃=cyclohexane dicarboxylic acid, such that the ratio of polymerized fatty acid to CHDA is 5 to 1 or greater; and
n=20, such that the ratio of (—O—R₂—O—) to (—NH—R₂—NH—) is 3 to 1

Class II, Type B, CHDA (+ dimer), PAODA+PGDO, Terminated by PAOMA (PAOMA Terminated PGPEA (PAOMATPGPEA with CHDA)

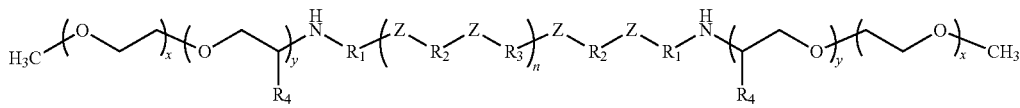

where:
R₁=polymerized fatty acid, hydrogenated or non-hydrogenated;
Z=O or NH;
R₂=poly(alkyleneoxy)moiety if Z=O;
or R₂=2-12 carbon straight chain or branched alkyl moiety if Z=NH;
R₃=polymerized fatty acid, hydrogenated or non-hydrogenated; and
or R₃=cyclohexane dicarboxylic acid, such that the ratio of polymerized fatty acid to CHDA is 5 to 1 or greater;
n=20, such that the ratio of (—O—R₂—O—) to (—NH—R₂—NH—) is 3 to 1;
R₄=H for (EO), or CH₃ for (PO);
x=ethylene oxide (EO) groups;
y=ethylene oxide (EO) groups where R₄=H; and
or y=propylene oxide (PO) groups where R₄=CH₃.

Class II, Type C, CHDA (+ dimer), PAODA+PGDO, Terminated by PGMO
(PGMO Terminated PGPEA (PGMOTPGPEA) with CHDA)

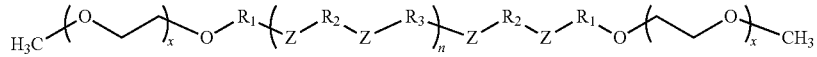

where:
R₁=polymerized fatty acid, hydrogenated or non-hydrogenated;
Z=O or NH;
R₂=poly(alkyleneoxy)moiety if Z=O;
or R₂=2-12 carbon straight chain or branched alkyl moiety if Z=NH;
R₃=polymerized fatty acid, hydrogenated or non-hydrogenated;
or R₃=cyclohexane dicarboxylic acid, such that the ratio of polymerized fatty acid to CHDA is 5 to 1 or greater;
n=20, such that the ratio of (—O—R₂—O—) to (—NH—R₂—NH—) is 3 to 1; and
x=15.

TABLE 1

Non-limiting examples of Possible PGPEA Components

| Component | Abbrev'n | Structure | Examples |
|---|---|---|---|
| Dimer Acid | Dimer | Hydrogenated or non-hydrogenated | P-1006 - PRIPOL ® 1006 hydrogenated polymerized fatty acid (Uniqema)<br>E-1008 - EMPOL ® 1008 hydrogenated polymerized fatty acid (Cognis)<br>U-18 - UNIDYME ® 18 polymerized fatty acid (Arizona) |

TABLE 1-continued

Non-limiting examples of Possible PGPEA Components

| Component | Abbrev'n | Structure | Examples |
|---|---|---|---|
| Cyclohexane Dicarboxylic Acid | CHDA | 1,4-HOOC—($C_6H_4$)—COOH | Eastman CDA |
| Ethylene diamine | EDA | $H_2N$—$CH_2CH_2$—$NH_2$ | |
| Polyalkylene glycol diol | PGDO | HO-(PAO)-OH | PEG600 - Polyethylene glycol, 750 mol. wt.; PEG1500 - Polyethylene glycol, 1500 mol. wt.; PEG2000 - Polyethylene glycol, 2000 mol. wt. (all from Dow) |
| Polyalkylene glycol ether-alcohol | PGMO | $R^1$O-(PAO)-OH | MPEG750 - Methoxy polyethylene glycol, 750 molecular weight (Dow); Dipropylene glycol mono-methyl ether (DPGME) |
| Polyalkyleneoxy diamine | PAODA | $H_2N$-(PAO)-$NH_2$ | JEFFAMINE ® D-400, D-2000, XTJ-500, XTJ-502 (Huntsman) |
| Polyalkyleneoxy monoamine | PAOMA | $R^2$O-(PAO)-$NH_2$ | JEFFAMINE ® M-2070, M-506 (Huntsman) |

Example 2

Preparation of PGPEA Gellants

Because esterification is slower than amidification, a typical PGPEA synthesis takes about 16-20 hours at 215° C. under nitrogen sweep.

Tables 2 and 3 list components and properties of several example PGPEAs. Class I PGPEAs having as chain extender segments blocks derived from polyethylene glycol (PEG) generally are hydrophilic. Five examples of such PGPEAs were produced and their compositions and properties are provided in Table 2. If a polypropylene glycol (PPG) is utilized as the PGDO, then the resulting polymer generally is hydrophobic. Four examples of hydrophobic Class I and Class II PGPEAs were produced and their compositions and properties are provided in Table 3. Each of these PGPEAs are flexible, clear solids having satisfactory softening points and relatively high molecular weights.

The PGPEAs listed in Tables 2 and 3 were prepared similarly except for their individual components. For example, to prepare PGPEA #464-27, a flask equipped with an agitator, thermocouple probe, nitrogen inlet, and condenser was charged with polymerized fatty acid (PRIPOL® 1006, Uniqema Corporation, 51.6 weight %, 100 equiv.% acid groups), polyethyleneglycol of molecular weight 600 (Dow Corporation, 15.0 wt %, 28.0 equivalent % of all amine and alcohol groups), ethylene diamine (3.4 weight %, 62.3 equivalent % of all amine and alcohol groups), terminating monoamine (Huntsman JEFFAMINE® M2070, 30.0 weight %, 8.2 equiv. % of all amine and alcohol groups), and a small amount of hypophosphorous acid (ca. 0.1% as a 25% aqueous solution). The mixture was slowly heated with agitation and with removal of water-of-reaction to 210-215° C. and held at that temperature for 16 hours. The mixture was then cooled to about 150° C. and poured out. As indicated in Table 2, Product #464-27 is a flexible, clear, near water-white solid having a softening point of 96.8° C. and a weight-average molecular weight of 26,960.

TABLE 2

Compositions and Properties of Class I, Water-Friendly PGPEAs

| POLYMER CLASS | Class I, Type A | Class I, Type C | Class I, Type C | Class I, Type B | Class I, Type B |
|---|---|---|---|---|---|
| NUMBER | 464-31 | 464-29 | 464-33 | 464-27 | 464-34 |
| COMPONENTS | | | | | |
| DiAcid | P-1006 | E-1008 | U-18 | P-1006 | P-1006 |
| Terminator | None | MPEG750 | MPEG750 | M-2070 | M-2070 |
| PGDO (diol) | PEG 1500 | PEG 600 | PEG 1500 | PEG 600 | PEG 1500 |
| DiAmine | EDA | EDA | EDA | EDA | EDA |
| CHARGE (Wt. %) | | | | | |
| DiAcid | 46.3% | 54.0% | 49.3% | 51.6% | 39.5% |
| Terminator | 0.0% | 24.0% | 7.6% | 30.0% | 27.5% |
| PGDO (diol) | 50.9% | 19.3% | 39.9% | 15.0% | 30.5% |
| DiAmine | 2.78% | 2.7% | 3.20% | 3.4% | 2.5% |
| Total Wt % PAO | 50.9% | 43.3% | 47.5% | 45.0% | 58.0% |
| Equivalent % Bases | | | | | |
| Terminator | 0.0% | 17.4% | 6.0% | 8.2% | 9.8% |
| PGDO (diol) | 42.2% | 34.3% | 31.1% | 28.0% | 29.7% |
| DiAmine | 56.7% | 47.2% | 61.4% | 62.3% | 59.8% |
| Total Equiv. % Ester | 42.2% | 51.7% | 37.1% | 28.0% | 29.7% |
| PROPERTIES | | | | | |
| Acid Number | 7.5 | 6.8 | 11.7 | 5.4 | 9.1 |
| Amine Number | 1 | 0.9 | 2.2 | 1.5 | 1.8 |
| Softening Point | 94.5 | 90.7 | 91.8 | 96.8 | 96.8 |
| Wt. Aver. Mol. Wt. | 35,850 | 17,890 | 21,970 | 26,960 | 23,790 |

TABLE 3

Compositions and Properties of Oil-Friendly PGPEAs of Classes I & II

| POLYMER CLASS | Class I, Type A | Class I, Type B | Class I, Type B | Class I, Type C | Class II, Type A |
|---|---|---|---|---|---|
| NUMBER | 464-32 | 464-36 | 464-37 | 464-42 | 464-52 |
| COMPONENTS | | | | | |
| DiAcid | P-1006 | P-1006 | P-1006 | P-1006 | CHDA |
| Terminator | None | MPEG750 | DPGME | M-2070 | none |
| PGDO | PPG 1000 | PPG 2000 | PPG 2000 | PPG 2000 | PPG 2000 |
| DiAmine | EDA | EDA | EDA | EDA | D400 |
| CHARGE (Wt. %) | | | | | |
| DiAcid | 52.0% | 41.5% | 46.3% | 35.5% | 19.1% |
| Terminator | 0.0% | 12.5% | 3.0% | 45.0% | |
| PGDO | 45.2% | 43.5% | 47.9% | 17.0% | 40.0% |
| DiAmine | 2.71% | 2.50% | 2.77% | 2.5% | 40.9% |
| Equivalent % Bases | | | | | |
| Terminator | 0.0% | 11.8% | 12.7% | 17.9% | — |
| PGDO | 50.1% | 30.2% | 29.7% | 13.8% | 18.0% |
| DiAmine | 49.3% | 56.9% | 56.5% | 66.5% | 83.7% |
| Properties | | | | | |
| Acid Number | 6.9 | 9.8 | 8.9 | 10.3 | 6.9 |
| Amine Number | 1.4 | 1 | 1.4 | 0.6 | 0.7 |
| Softening Point | 93.5 | 94.1 | 99.9 | 87.5 | 122.9 |
| Wt. Aver. Mol. Wt. | 50,290 | 22,090 | nd | 14,050 | 12,710 |

Examples of Class II PGPEAs were also made, two with hydrophilic character (shown in Table 4) and one with hydrophobic character (shown in Table 3). Table 4 shows compositions and properties of non-limiting examples of Class II water-friendly PGPEAS, each of which are flexible clear solids. One of these (#230-93) had a softening point under 100° C. As known by one of skill in the art, the softening point of any given composition may be reduced by increasing the dimer acid content (and lowering the CHDA content).

Example 3

Testing and Assessing Gelability

Gelation ability of the PGPEA polymers of Tables 2, 3 and 4 were tested at 10% solids using the following procedure: 1.00 g of resin and 9.00 g of solvent were charged to a glass vial, a small magnetic stirrer added, and the cap screwed on loosely. The vial was placed on a hot plate set to mild heat (adjusted so that the liquid mixture could not go over about 100° C.) and allowed to stir with heating for about 30 minutes (until the resin melted and the mixture became homogeneous, if not clear). The vial was then removed, agitated while still hot on a vortex stirrer briefly to ensure good resin contact with the solvent, and allowed to cool to room temperature without agitation (to avoid incorporation of gas bubbles). If the resin did not fully dissolve after this treatment, the heating cycle was repeated for about 10-15 minutes more.

TABLE 4

Compositions and Properties of Class II, Water-Friendly Polyglycol Poly(ester-amides)

| POLYMER CLASS | Class II, Type A | Class II, Type A | Class II, Type A | Class II, Type A | Class II, Type A |
|---|---|---|---|---|---|
| NUMBER | 230-93 | 230-94 | 245-75 | 464-49 | 464-55 |
| ACIDS | | | | | |
| DiAcid | 1,4-CHDA | 1,4-CHDA | 1,4-CHDA | 1,4-CHDA | 1,4-CHDA |
| Second DiAcid | Empol | Empol | Empol | None | None |

TABLE 4-continued

Compositions and Properties of Class II, Water-Friendly Polyglycol Poly(ester-amides)

| POLYMER CLASS | Class II, Type A | Class II, Type A | Class II, Type A | Class II, Type A | Class II, Type A |
|---|---|---|---|---|---|
| BASES | | | | | |
| PGDO | PEG600 | PEG600 | PEG600 | PEG1500 | PEG1500 |
| DiAmine | D-400 | D-400 | D-400 | D-400 | D-400 |
| CoDiamine/Polyol | | Glycerol | | | D-2000 |
| Weight % Acids | | | | | |
| DiAcid | 20.1% | 19.9% | 21.5% | 20.2% | 16.9% |
| Second DiAcid | 13.4% | 14.9% | 10.7% | | |
| Weight % Bases | | | | | |
| Poly Glycol | 18.4% | 14.8% | 21.5% | 39.5% | 32.0% |
| DiAmine | 48.1% | 50.1% | 46.3% | 40.4% | 28.2% |
| CoDiamine/Polyol | | 0.4% | | | 22.9% |
| PAO Total | 66.5% | 64.8% | 67.8% | 79.8% | 60.2% |
| Equivalent % Acids | | | | | |
| DiAcid | 83.3% | 81.8% | 87.0% | 100.0% | 100.0% |
| Second DiAcid | 16.7% | 18.2% | 13.0% | 0.0% | 0.0% |
| Equivalent % Bases | | | | | |
| Poly Glycol | 21.9% | 17.4% | 25.0% | 22.5% | 21.7% |
| DiAmine | 78.1% | 78.6% | 73.5% | 78.3% | 65.3% |
| CoDiamine/Polyol | | 4.1% | | | 11.7% |
| PROPERTIES | | | | | |
| Acid Number | 7.7 | 13.3 | 9.9 | 4.6 | 4.5 |
| Amine Number | 4.4 | 0.9 | 0.6 | 0.1 | 1.2 |
| Softening Point | 96.9 | 117.3 | 107.6 | 112.7 | 107.0 |
| Weight Aver. MW | n.d. | n.d. | n.d. | 16,425 | 17,269 |

When evaluating a candidate polymer as a gellant, generally two questions are addressed: 1) With how wide a range of liquids does it form a quality gel? and 2) How low is the use level needed to form a quality gel?

The quality of a gel is judged by its firmness and its clarity and this is done qualitatively, by simple inspection. Both indicators are important. Clarity of a gel-liquid blend increases with increasing resin-liquid compatibility, but if the polymer cannot form an adequate H-bonding network, no gelation occurs and the blend remains (upon cooling) a simple polymer solution. Gels made with many E/ATPAs exhibit increasing haze (increasing incompatibility) upon dilution.

Cooled resin solutions are judged by shaking them or probing them with a wooden stir stick and rated with the following designations:

"Gel"—Solution does not flow or slump when inverted and shaken strongly

"Jelly"—Solution slumps, or cracks when shaken

"Paste"—Mixture is very cloudy and inhomogeneous, slumps or flows easily when stirred.

"Incompatible"—No gel, resin can be seen as large aggregates or a separate phase.

"Solution"—Solution is fluid (low viscosity)

Cooled resin solutions are judged by eye for clarity and rated with the following designations:

No notation—Solution is as clear as a true solution.

"Slightly Hazy"—Solution is not as clear as a true solution but some fogging is obvious.

"Hazy"—Solution is foggy but print is legible when viewed through the solution.

"Cloudy"—Cannot see through the solution at all.

Table 5 provides the gelation ability results for PGPEAs at 10%.

TABLE 5

Gelation Ability Results For Polyethylene Glycol)-Based Poly(Ester-Amides) at 10%

| POLYMER CLASS | Class I, Type A | Class I, Type C | Class I, Type C | Class I, Type B | Class I, Type B |
|---|---|---|---|---|---|
| NUMBER | 464-31 | 464-29 | 464-33 | 464-27 | 464-34 |
| Total Wt % PEO | 50.9% | 43.3% | 47.5% | 45.0% | 58.0% |
| Wt. % Terminator | 0.0% | 24.0% | 7.6% | 30.0% | 27.5% |
| TEST LIQUID | | | | | |
| Water | Incompatible | Incompatible | White cream | Blue paste | Solution, soapy |
| 1:1 PG:Water | Incompatible | Jelly, trans. | Gel | Gel | Solution |
| PEG200 | Incompatible | n.d. | Incompatible | Incompatible | Incompatible |
| Propylene Glycol | Incompatible | Incompatible | Incompatible | Gel | Solution, cloudy |

TABLE 5-continued

Gelation Ability Results For Polyethylene Glycol)-Based Poly(Ester-Amides) at 10%

| POLYMER CLASS | Class I, Type A | Class I, Type C | Class I, Type C | Class I, Type B | Class I, Type B |
|---|---|---|---|---|---|
| Tripropylene Glycol | Gel, sl. haze | Gel, cloudy | Gel, sl. haze | Gel, sl. haze | Gel |
| Polypro'lene Glycol 425 | Gel | Gel | Gel | Gel | Gel |
| DPG Mono Me Ether | Gel, soft | Gel | Jelly, very weak | Gel | Jelly, weak |
| DPG Di Me Ether | Gel | Gel | Gel | Gel | Gel |
| High-HLB Surfactant | Gel | Gel | Gel | Gel | Gel |
| Medium-HLB Surfactant | Gel | Jelly | Jelly | Gel | Jelly |
| Propylene Carbonate | Chunky, pasty | Gel, hazy | Cloudy pasty | Gel, sl. haze | Gel |
| Octyl Salicylate | Gel | Gel | Gel, trans. | Gel | Gel |
| Methyl Isobutyl Ketone | Gel | Jelly, weak | Jelly | Gel | Jelly |
| Dimethyl Adipate | Gel | Gel | Gel | Gel | Gel |
| Ethyl Hexyl Acetate | Gel, cloudy | Gel. | Cloudy pasty | Gel | Gel |

Preferred test liquids vary with changing marketing interests but usually include water, glycols, water-glycol blends, propylene carbonate, and glycol ethers for the "water-friendly" gellant candidates and octyl salicylate, dibutyl adipate, polypropylene glycol 425, ethyl lactate, 2-ethyl-hexyl acetate, and methyl isobutyl ketone for the medium-polarity liquid gellant candidates. Another criterion for the quality of a candidate resin is the stability (over time, temperature, etc.) of a gel it forms. For example, we greatly prefer gels that do not exhibit syneresis, hazing, or cracking during storage, heating, or cooling. For some applications, we need gels to pass high temperature tests. For this study, we did not carry out stability testing. PGPEA polymers based on poly(ethylene glycol) exhibited some ability to affect the rheology of relatively polar liquids including propylene glycol, water, and mixtures of glycol and water. Test results for 10 wt % loadings of these polymers in various polar liquids (10% polymer, 90% test liquid) are provided in Table 5.

In Table 6, the four best performers are compared with SYLVACLEAR WF1500V, a PAOPA which is currently the best-performing commercial water-friendly gellant. In this comparison, polymer #464-27 does very well, out-performing WF1500.

TABLE 6

Gelation Ability of Four PGPEAs and SYLVACLEAR WF1500V

| NUMBER | WF1500V | 464-29 | 464-33 | 464-27 | 464-34 |
|---|---|---|---|---|---|
| Water | Blue Soln. | Incompatible | White cream | Blue paste | Solution, soapy |
| 1:1 PG:Water | Gel | Jelly, trans. | Gel | Gel | Solution |
| Propylene Glycol | Gel (hzy) | Incompatible | Incompatible | Gel | Solution, cloudy |
| Tripropylene Glycol | Gel | Gel, cloudy | Gel, sl. haze | Gel, sl. haze | Gel |
| DPG Mono Me Ether | V.Wk.Jelly | Gel | Jelly, very weak | Gel | Jelly, weak |
| DPG Di Me Ether | V.Wk.Jelly | Gel | Gel | Gel | Gel |
| Propylene Carbonate | Gel, sl. Haze | Gel, hazy | Cloudy pasty | Gel, sl. haze | Gel |
| Octyl Salicylate | Gel | Gel | Gel, trans. | Gel | Gel |
| Dimethyl Adipate | Gel (cldy) | Gel | Gel | Gel | Gel |
| Ethyl Hexyl Acetate | Soluble | Gel | Cloudy pasty | Gel | Gel |

PGPEA polymers based on poly(propylene glycol) exhibited some ability to affect the rheology of low-to-medium polarity liquids, including esters, ketones, and ethers. Test results are listed in Table 7. One interesting resin of Table 7 is Polymer #464-37 which stands out as the best performer, rivaling the performance of SYLVACLEAR PE1800V.

The performance of the Class II (CHDA-based) polymers was also compared against the two developmental leading water-friendly gellants SYLVACLEARs PE400 and WF1500V and the results are provided in Table 8. One interesting resin of Table 8 is #464-49 because it gels a 1:1 mixture of water and glycerol and even forms a weak jelly in water itself.

TABLE 7

Gelation Ability Results For Polypropylene Glycol-Based Poly(Ester-Amides)

| POLYMER CLASS | Class I, Type A | Class I, Type B | Class I, Type B | Class I, Type C | Class II, Type A |
|---|---|---|---|---|---|
| NOTEBOOK NUMBER | 464-32 | 464-36 | 464-37 | 464-42 | 464-52 |
| Wt. % Terminator | 0.0% | 12.5% | 3.0% | 45.0% | 0.0% |
| Wt. % PPG Diol | 45.2% | 43.5% | 47.9% | 17.0% | 40.0%* |
| TEST LIQUID | | | | | |
| Polypropylene Glycol 425 | Gel, cloudy | Gel | Gel | Gel, sl. hazy | Gel, hazy |
| DPG Mono Me Ether | Jelly, weak | Weak Jelly | Gel | Solution | Solution |
| DPG Di Me Ether | Gel | Gel | Gel | Jelly, weak | Paste, cloudy |
| High-HLB Surfactant | Solution | Gel | Solution | Gel | Soln, cloudy |
| Medium-HLB Surfactant | Gel | Jelly | Gel | Solution | Gel |
| Octyl Salicylate | Gel | Gel | Gel | Jelly, weak | Pasty, trnslucnt |
| Methyl Isobutyl Ketone | Jelly | Jelly, weak | Gel | Solution | Paste, hazy |
| Dimethyl Adipate | Gel, cloudy | Gel | Gel | Gel | Gel, cloudy |
| Ethyl Hexyl Acetate | Gel | Gel | Gel | Jelly, weak | Paste, cloudy |
| Isopropyl Myristate | Gel | Gel | Gel | Paste, cloudy | Part. sol. weak |
| Isopropyl Myristate:Mineral Oil Blend (2:1) | Cloudy pasty | Liquid, two phases | Gel | Incompatible | Incompatible |

*also contained 40.9% D400 as the diamine portion

TABLE 8

Gelation Ability of Three PGPEAs and SYLVACLEARs PE400 and WF1500V

| Notebook Number | 464-49 | 464-55 | 464-54* | PE400 | WF1500 |
|---|---|---|---|---|---|
| Wt % PEO Diol/Diamine | 39.5% | 32.0% | 25.0% | 15.0% | 47.5%# |
| Wt % PPG Diamine | 40.4% | 51.1% | 35.5% | 51.1% | — |
| Water:Glycerol 1:1 | Gel | Solution | Soln (milky) | Incompat. | Cloudy disp . . . |
| Water:Glycerol:PG'ol 1:1:1 | Jelly | n.d | Soln (milky) | Incompat. | n.d |
| Water | Jelly (v. wk) | Solution | Sol'n (foamy) | Sol'n(cloudy) | Blue Soln. |
| PEG 200 | Gel | | Incompat. | Soln.(hazy) | Incompat. |
| 1:1 NMP:Water | Solution | Solution | Soln.(blsh, vis.) | Soln (cloudy) | Gel |
| 1:1 PG:Water | Solution | Solution | Soln part (hzy) | Soln, partial | Gel |
| Propylene Glycol | Solution | Solution | Sol'n, part. | Solution | Gel (hzy) |
| Tripropylene Glycol | Solution | Solution | Solution | Sol'n (visc.) | Gel |
| PPG425 | Gel | Jelly | Gel | Gel | Gel |
| Propylene Carbonate | Gel | Gel | Incomp. | Incompat. | Gel (sl.hzy) |
| Octyl Salicylate | Cloudy pasty | Jelly (hazy) | Part.gel, trans l. | Sol'n, partial | Gel |
| Ethoxyethyl Propionate | Gel (sl. hazy) | Part.soln, lqud | n.d | n.d. | Gel |

*Not a PGPEA; reaction product of CHDA, 13.5%, dimer acid, 26.0%, XTJ-500 25%, and D400, 35.5%
Contains 29.7% monoamine terminator as M-2070.

All references mentioned herein including U.S. patents, published U.S. patent application, U.S. patent applications, foreign patents, foreign patent applications and non-patent publications, for example, IPCOM documents, are incorporated herein by reference, in their entirety.

From the foregoing it will be appreciated that, although specific embodiments of the invention have been described herein for purposes of illustration, various modifications may be made without deviating from the spirit and scope of the invention.

I claim:

1. A polyether poly(ester-amide) block copolymer comprising at least one structure selected from the group consisting of structure I, structure II, structure III, structure IV, structure V and structure VI:

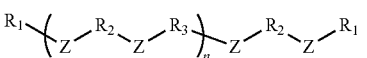

structure I wherein $R_1$=polymerized fatty acid, hydrogenated or non-hydrogenated;

Z=O or NH;

$R_2$=poly(alkyleneoxy)moiety if Z=O, or $R_2$=2-12 carbon straight chain or branched alkyl moiety if Z=NH; and n=20, such that the ratio of (—O—$R_2$—O—) to (—NH—$R_2$—NH—) is 3 to 1;

structure II

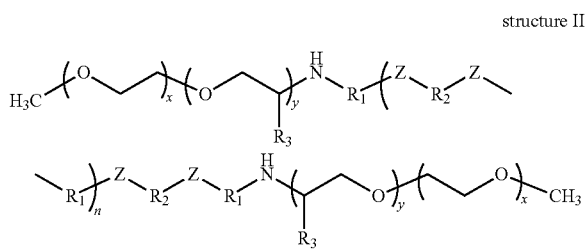

wherein $R_1$=polymerized fatty acid, hydrogenated or non-hydrogenated;
Z=O or NH;
$R_2$=poly(alkyleneoxy)moiety if Z=O;
or $R_2$=2-12 carbon straight chain or branched alkyl moiety if Z=NH;
n=20, such that the ratio of (—O—$R_2$—O—) to (—NH—$R_2$—NH—) is 3 to 1;
x=ethylene oxide (EO) groups;
y=ethylene oxide (EO) groups where $R_3$=H;
or y=propylene oxide (PO) groups where $R_3$=CH$_3$; and
$R_3$=H for (EO), or CH$_3$ for (PO);

structure III

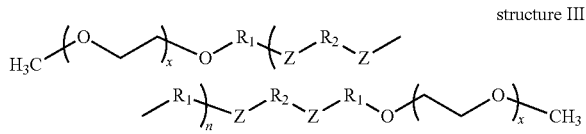

wherein $R_1$=polymerized fatty acid, hydrogenated or non-hydrogenated;
Z=O or NH;
$R_2$=poly(alkyleneoxy) moiety if Z=O;
or $R_2$=2-12 carbon straight chain or branched alkyl moiety if Z=NH;
n=20, such that the ratio of (—O—$R_2$—O—) to (—NH—$R_2$—NH—) is 3 to 1; and
x=15;

structure IV

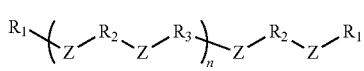

wherein $R_1$=polymerized fatty acid, hydrogenated or non-hydrogenated;
Z=O or NH;
$R_2$=poly(alkyleneoxy)moiety if Z=O;
or $R_2$=2-12 carbon straight chain or branched alkyl moiety if Z=NH;
$R_3$=polymerized fatty acid, hydrogenated or non-hydrogenated;
or $R_3$=cyclohexane dicarboxylic acid, such that the ratio of polymerized fatty acid to CHDA is 5 to 1 or greater; and
n=20, such that the ratio of (—O—$R_2$—O—) to (—NH—$R_2$—NH—) is 3 to 1;

structure V

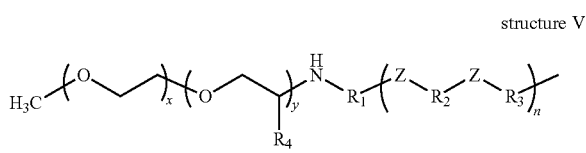

-continued

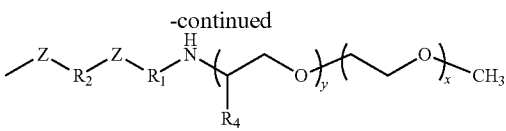

wherein $R_1$=polymerized fatty acid, hydrogenated or non-hydrogenated;
Z=O or NH;
$R_2$=poly(alkyleneoxy)moiety if Z=O;
or $R_2$=2-12 carbon straight chain or branched alkyl moiety if Z=NH;
$R_3$=polymerized fatty acid, hydrogenated or non-hydrogenated;
or $R_3$=cyclohexane dicarboxylic acid, such that the ratio of polymerized fatty acid to CHDA is 5 to 1 or greater;
n=20, such that the ratio of (—O—$R_2$—O—) to (—NH—$R_2$—NH—) is 3 to 1;
$R_4$=H for (EO), or CH$_3$ for (PO);
x=ethylene oxide (EO) groups; and
y=ethylene oxide (EO) groups where $R_4$=H;
or y=propylene oxide (PO) groups where $R_4$=CH$_3$;

and structure VI

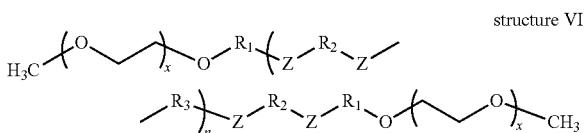

wherein $R_1$=polymerized fatty acid, hydrogenated or non-hydrogenated;
Z=O or NH;
$R_2$=poly(alkyleneoxy)moiety if Z=O;
or $R_2$=2-12 carbon straight chain or branched alkyl moiety if Z=NH;
$R_3$=polymerized fatty acid, hydrogenated or non-hydrogenated;
or $R_3$=cyclohexane dicarboxylic acid, such that the ratio of polymerized fatty acid to CHDA is 5 to 1 or greater;
n=20, such that the ratio of (—O—$R_2$—O—) to (—NH—$R_2$—NH—) is 3 to 1; and
x=15.

2. The copolymer of claim 1 comprising a weight average molecular weight of between 10,000 and 40,000, as measured using gel permeation chromatography with polystyrene as reference standards.

3. The copolymer of claim 1 comprising poly(alkyleneoxy) (PAO)-containing components in the range of about 20-50 wt %.

4. The copolymer of claim 1 comprising a softening point between 60° C. and 180° C., and formed from a reaction mixture comprising: i) a diacid, ii) a diamine, and iii) a poly(alkyleneoxy)polyol, wherein said diacid is selected from the group consisting of polymerized fatty, cyclohexane dicarboxylic acids, and any combination thereof; and wherein said diamine is selected from the group consisting of short chain aliphatic diamines having 2-6 carbons, poly(alkyleneoxy)diamines, and any combination thereof.

5. The copolymer of claim 4 wherein said reactants further comprise one or more monofunctional compound(s) reactive with carboxylic acid or amine groups, and wherein said at least one structure is selected from the group consisting of structure II, structure III, structure V and structure VI.

6. The copolymer of claim 4 wherein said diacid is polymerized fatty acid, wherein said diamine is a short chain aliphatic diamine having 2-6 carbons, and wherein said at least one structure is selected from the group consisting of structure I, structure II and structure III.

7. The copolymer of claim 4 wherein said diacid is a cyclohexane dicarboxylic acid, wherein said diamine is a poly(alkyleneoxy)diamine, and wherein said at least one structure is selected from the group consisting of structure IV, structure V and structure VI.

8. A composition comprising a) a copolymer of claim 1, and b) a compound, where the compound is a liquid at room temperature in neat form.

9. The composition of claim 8 wherein said composition is a gel.

10. The composition of claim 8 wherein the compound comprises at least one chemical group selected from ester, ether, halogen, carbonate and sulfoxide.

11. A process for preparing a block copolymer comprising reacting together reactants comprising: i) a diacid, ii) a diamine, and iii) a poly(alkyleneoxy)polyol, wherein said diacid is selected from the group consisting of polymerized fatty, cyclohexane dicarboxylic acids, and any combination thereof, and wherein said diamine is selected from the group consisting of short chain aliphatic diamines having 2-6 carbons, poly(alkyleneoxy)diamines, and any combination thereof, wherein the block copolymer includes ($-O-R_2-O-$) groups and ($-NH-R_2-NH-$) groups and the ratio of ($-O-R_2-O-$) groups to ($-NH-R_2-NH-$) groups is 3 to 1.

12. The process of claim 11 wherein said block copolymer comprises at least one structure selected from the group consisting of structure I, structure II, structure III, structure IV, structure V and structure VI:

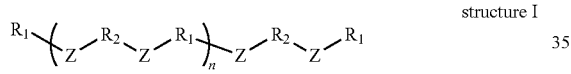

structure I wherein $R_1$=polymerized fatty acid, hydrogenated or non-hydrogenated;
Z=O or NH;
$R_2$=poly(alkyleneoxy)moiety if Z=O,
or $R_2$=2-12 carbon straight chain or branched alkyl moiety if Z=NH; and
n=20, such that the ratio of ($-O-R_2-O-$) to ($-NH-R_2-NH-$) is 3 to 1;

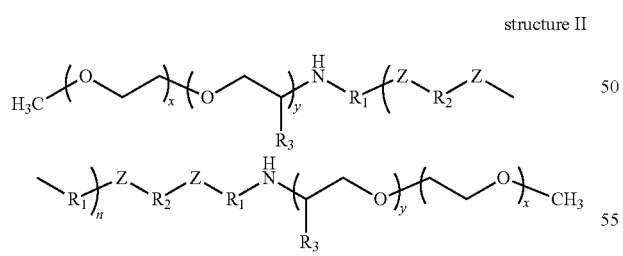

structure II wherein $R_1$=polymerized fatty acid, hydrogenated or non-hydrogenated;
Z=O or NH;
$R_2$=poly(alkyleneoxy)moiety if Z=O;
or $R_2$=2-12 carbon straight chain or branched alkyl moiety if Z=NH;
n=20, such that the ratio of ($-O-R_2-O-$) to ($-NH-R_2-NH-$) is 3 to 1;
x=ethylene oxide (EO) groups;
y=ethylene oxide (EO) groups where $R_3$=H;
or y=propylene oxide (PO) groups where $R_3$=CH$_3$; and
$R_3$=H for (EO), or CH$_3$ for (PO);

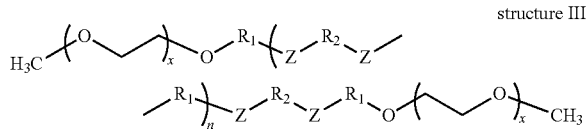

structure III wherein $R_1$=polymerized fatty acid, hydrogenated or non-hydrogenated;
Z=O or NH;
$R_2$=poly(alkyleneoxy) moiety if Z=O;
or $R_2$=2-12 carbon straight chain or branched alkyl moiety if Z=NH;
n=20, such that the ratio of ($-O-R_2-O-$) to ($-NH-R_2-NH-$) is 3 to 1; and
x=15;

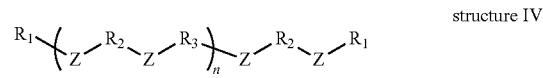

structure IV wherein $R_1$=polymerized fatty acid, hydrogenated or non-hydrogenated;
Z=O or NH;
$R_2$=poly(alkyleneoxy)moiety if Z=O;
or $R_2$=2-12 carbon straight chain or branched alkyl moiety if Z=NH;
$R_3$=polymerized fatty acid, hydrogenated or non-hydrogenated;
or $R_3$=cyclohexane dicarboxylic acid, such that the ratio of polymerized fatty acid to CHDA is 5 to 1 or greater; and
n=20, such that the ratio of ($-O-R_2-O-$) to ($-NH-R_2-NH-$) is 3 to 1;

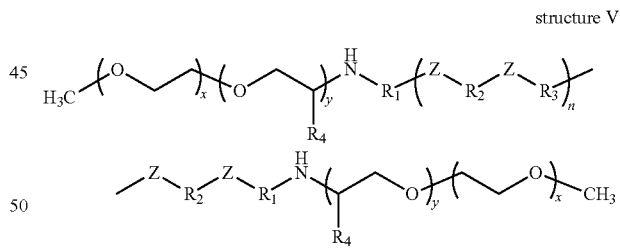

structure V wherein $R_1$=polymerized fatty acid, hydrogenated or non-hydrogenated;
Z=O or NH;
$R_2$=poly(alkyleneoxy)moiety if Z=O;
or $R_2$=2-12 carbon straight chain or branched alkyl moiety if Z=NH;
$R_3$=polymerized fatty acid, hydrogenated or non-hydrogenated or $R_3$=cyclohexane dicarboxylic acid, such that the ratio of polymerized fatty acid to CHDA is 5 to 1 or greater;
n=20, such that the ratio of ($-O-R_2-O-$) to ($-NH-R_2-NH-$) is 3 to 1;
$R_4$=H for (EO), or CH$_3$ for (PO);

x=ethylene oxide (EO) groups; and
y=ethylene oxide (EO) groups where $R_4$=H;
or y=propylene oxide (PO) groups where $R_4$=$CH_3$;

and

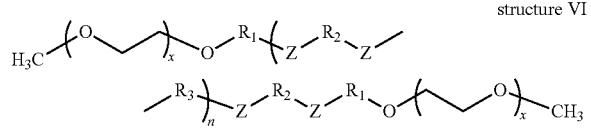

structure VI wherein $R_1$=polymerized fatty acid, hydrogenated or non-hydrogenated;
Z=O or NH;
$R_2$=poly(alkyleneoxy)moiety if Z=O;
or $R_2$=2-12 carbon straight chain or branched alkyl moiety if Z=NH;
$R_3$=polymerized fatty acid, hydrogenated or non-hydrogenated;
or $R_3$=cyclohexane dicarboxylic acid, such that the ratio of polymerized fatty acid to CHDA is 5 to 1 or greater;
n=20, such that the ratio of (—O—$R_2$—O—) to (—NH—$R_2$—NH—) is 3 to 1; and x=15.

13. The process of claim 12 wherein said poly(alkyleneoxy)polyol is at least one selected from the group consisting of di-, tri-, tetra-ethylene glycols, di-, tri-, tetra-propylene glycol, di-, tri-, tetra-butylene glycols, and higher molecular weight poly(ethylene glycol)s, poly(propylene glycol)s, poly(butylenes glycol)s, mixed poly(ethyleneoxy-co-propyleneoxy)glycol polymers, and any combination thereof.

14. The process of claim 13 wherein said reactants further comprise one or more monofunctional compound(s) reactive with carboxylic acid or amine groups, and wherein said at least one structure is selected from the group consisting of structure II, structure III, structure V and structure VI.

15. The process of claim 13 wherein said diacid is polymerized fatty acid, wherein said diamine is a short chain aliphatic diamine having 2-6 carbons, and wherein said at least one structure is selected from the group consisting of structure I, structure II and structure III.

16. The process of claim 13 wherein said diacid is a cyclohexane dicarboxylic acid, wherein said diamine is a poly(alkyleneoxy)diamine, and wherein said at least one structure is selected from the group consisting of structure IV, structure V and structure VI.

17. A method for preparing a gel comprising combining at elevated temperature a copolymer of claim 1 with a liquid having hydroxyl and/or ether functionality to provide a mixture, and allowing the mixture to cool to room temperature to form a gel.

18. An article of manufacture comprising a copolymer of claim 1.

19. The article of claim 18 formulated as any one or more of the group consisting of a fragrance stick, an air freshener, a fragrance gel, a personal care product comprising at least one physiologically acceptable oil, and any combination thereof.

20. The article of claim 18 further comprising at least one of the group consisting of surfactants, colorants, fragrances, and any combination thereof.

* * * * *